US006687523B1

(12) United States Patent
Jayaramen et al.

(10) Patent No.: US 6,687,523 B1
(45) Date of Patent: *Feb. 3, 2004

(54) FABRIC OR GARMENT WITH INTEGRATED FLEXIBLE INFORMATION INFRASTRUCTURE FOR MONITORING VITAL SIGNS OF INFANTS

(75) Inventors: Sudaresan Jayaramen, Atlanta, GA (US); Sungmee Park, Tucker, GA (US); Rangaswamy Rajamanickam, Atlanta, GA (US); Chandramohan Gopalsamy, Tamil Nadu (IN)

(73) Assignee: Georgia Tech Research Corp., Atlanta, GA (US)

( * ) Notice: Subject to any disclaimer, the term of this patent is extended or adjusted under 35 U.S.C. 154(b) by 133 days.

This patent is subject to a terminal disclaimer.

(21) Appl. No.: 09/610,929

(22) Filed: Jul. 6, 2000

Related U.S. Application Data

(63) Continuation-in-part of application No. 09/273,175, filed on Mar. 19, 1999, now Pat. No. 6,381,482, and a continuation-in-part of application No. 09/157,607, filed on Sep. 21, 1998, now Pat. No. 6,145,551.
(60) Provisional application No. 60/142,360, filed on Jul. 6, 1999, provisional application No. 60/085,266, filed on May 13, 1998, and provisional application No. 60/059,444, filed on Sep. 22, 1997.

(51) Int. Cl.⁷ .................................................. A61B 5/04
(52) U.S. Cl. ........................ 600/388; 600/390; 600/534
(58) Field of Search ................................. 600/372, 373, 600/382–384, 391–393, 534, 538, 388–390; 607/152

(56) References Cited

U.S. PATENT DOCUMENTS

| | | | |
|---|---|---|---|
| 1,282,908 A | 10/1918 | Miller | |
| 2,579,383 A | 12/1951 | Goudsmit | |
| 2,935,096 A | 5/1960 | Cole | |
| 3,020,935 A | 2/1962 | Balis | |
| 3,409,007 A | 11/1968 | Fuller | |
| 3,483,861 A | 12/1969 | Tiep | |
| 3,534,727 A | 10/1970 | Roman | |
| 3,610,250 A | 10/1971 | Sarbacher | |
| 3,970,116 A | 7/1976 | Takada | |
| 4,016,868 A | 4/1977 | Allison | |
| 4,055,166 A | 10/1977 | Simpson et al. | |

(List continued on next page.)

FOREIGN PATENT DOCUMENTS

| | | |
|---|---|---|
| DE | 826183 | 7/1949 |
| DE | 29813614 U1 | 10/1998 |
| DE | 298 13 614 U | 10/1998 |
| FR | 2225560 | 11/1974 |
| FR | 2737651 | 2/1997 |
| FR | 2 737 651 A | 2/1997 |
| WO | WO99/64657 | 12/1999 |
| WO | WO 99 64657 A | 12/1999 |

OTHER PUBLICATIONS

Slide Presentation Titled High Velocity Penetration Analysis from the DLA/ARPA/NRaD Sensate Liner Workshop held Apr. 11, 1996; Author: Dr. Robert Eisler, MRC., Inc.
Slide Presentation Tilted Introducing Clarity Fit Technologies from the DLA/ARPA/NRaD Sensate LIner Workshop held Apr. 11, 1996; Author: Edith Gazzuolo, Clarity Inc.

(List continued on next page.)

Primary Examiner—Michael Peffley
(74) Attorney, Agent, or Firm—Thomas, Kayden, Horstemeyer & Risley LLP; Todd Deveau

(57) ABSTRACT

A garment for infants comprises a comfort component serving as a base, a plurality of signal transmission paths integrated within the comfort component; and at least one interface that provides a transmission path between the information infrastructure component and an external device. In addition, the garment has the means to ensure a snug fit for the baby so that the sensors stay in place to minimize the risk of false alarms while the baby is safe and comfortable. This feature also helps to extend the usable life of the garment as the baby grows.

23 Claims, 18 Drawing Sheets

U.S. PATENT DOCUMENTS

| | | | |
|---|---|---|---|
| 4,129,125 A | | 12/1978 | Lester et al. |
| 4,174,739 A | | 11/1979 | Rasero |
| 4,299,878 A | | 11/1981 | Rheaume |
| 4,308,872 A | | 1/1982 | Watson et al. |
| 4,572,197 A | | 2/1986 | Moore et al. |
| 4,580,572 A | * | 4/1986 | Granek et al. ............... 600/388 |
| 4,606,968 A | | 8/1986 | Thornton |
| 4,608,987 A | | 9/1986 | Mills |
| 4,668,545 A | | 5/1987 | Lowe |
| 4,708,149 A | | 11/1987 | Axelgaard |
| 4,722,354 A | | 2/1988 | Axelgaard |
| 4,726,076 A | | 2/1988 | Douez |
| 4,727,603 A | | 3/1988 | Howard |
| 4,729,377 A | | 3/1988 | Granek et al. |
| 4,730,625 A | | 3/1988 | Fraser et al. |
| 4,784,162 A | | 11/1988 | Ricks et al. |
| 4,815,473 A | * | 3/1989 | Watson et al. ............... 600/534 |
| 4,846,462 A | | 7/1989 | Regnier et al. |
| 4,889,131 A | | 12/1989 | Salem et al. |
| 4,960,118 A | | 10/1990 | Pennock |
| 5,038,782 A | | 8/1991 | Gevins |
| 5,103,504 A | | 4/1992 | Dordevic |
| 5,125,412 A | | 6/1992 | Thornton |
| 5,212,379 A | | 5/1993 | Nafarrate et al. |
| 5,224,479 A | | 7/1993 | Sekine |
| 5,241,300 A | * | 8/1993 | Buschmann ............. 340/573.1 |
| 5,263,491 A | | 11/1993 | Thornton |
| 5,316,830 A | | 5/1994 | Adams, Jr. et al. |
| 5,331,968 A | | 7/1994 | Williams et al. |
| 5,348,008 A | | 9/1994 | Bornn et al. |
| 5,353,793 A | | 10/1994 | Bornn |
| 5,374,283 A | * | 12/1994 | Flick .......................... 607/152 |
| 5,375,610 A | | 12/1994 | LaCourse et al. |
| 5,415,204 A | | 5/1995 | Kitamura |
| 5,436,444 A | | 7/1995 | Rawson |
| 5,450,845 A | | 9/1995 | Axelgaard |
| 5,454,376 A | | 10/1995 | Stephens et al. |
| 5,592,977 A | | 1/1997 | Kikuchi et al. |
| 5,610,528 A | | 3/1997 | Neely et al. |
| 5,624,736 A | | 4/1997 | DeAngelis |
| 5,636,378 A | | 6/1997 | Griffith |
| 5,694,645 A | | 12/1997 | Triplette |
| 5,701,370 A | | 12/1997 | Muhs et al. |
| 5,742,939 A | | 4/1998 | Williams |
| 5,749,365 A | * | 5/1998 | Magill ........................ 600/484 |
| 5,759,044 A | | 6/1998 | Redmond |
| 5,766,236 A | | 6/1998 | Detty |
| 5,802,611 A | | 9/1998 | McKenzie et al. |
| 5,817,035 A | | 10/1998 | Sullivan |
| 5,843,554 A | | 12/1998 | Katz |
| 5,864,291 A | | 1/1999 | Walton |
| 5,906,004 A | | 5/1999 | Lebby et al. |
| 5,913,830 A | | 6/1999 | Miles |
| 5,928,157 A | | 7/1999 | O'Dwyer |
| 5,944,669 A | | 8/1999 | Kaib |
| 5,963,891 A | | 10/1999 | Walker et al. |
| 6,047,203 A | | 4/2000 | Sackner et al. |
| 6,080,690 A | * | 6/2000 | Lebby et al. ................. 44/209 |
| 6,102,856 A | | 8/2000 | Groff et al. |
| 6,106,481 A | | 8/2000 | Cohen |
| 6,145,551 A | * | 11/2000 | Jayaramen et al. ............ 2/455 |
| 6,210,771 B1 | * | 4/2001 | Post et al. .................. 428/100 |
| 6,381,482 B1 | * | 4/2002 | Jayaraman et al. ......... 600/388 |

OTHER PUBLICATIONS

Slide Presentation Titled Silicone Rubber Fiber Optic Sensors from the DLA/ARPA/NRaD Sensate Liner Workshop held Apr. 11, 1996; Author: Jeffrey D. Muhs.

Slide Presentation Titled Vital Sign Sensing from the DLA/ARPA/NRaD Sensate Liner Workshop held Apr. 11, 1996; Author: Dr. Herman Watson, NIMS, Inc.

Slide Presentation Titled Sensate LIner Design & Development: Georgia Tech's Potential Contributions From the DLA/ARPA/NRathu D L Sensate LIner Workshop held Apr. 11, 1996; Author: Dr. Sundaresan Jayarama.

Slide Presentation Titled DEfense Logistics Agency Apparel Research Network Sensate Liner Workshop from DLA/ARPA/NRad held Apr. 11, 1996; Author: Donald O'Brien, Technical Enterprise Team.

Slide Presentation Titled TPSS/Senste Liner Technology Development from the DLA/ARPA/NRaD Sensate Liner Workshop held Apr. 11, 1996; Author Dr. Eric J. LInd.

Slide Presentation Titled Smart Textiles from the DLA/ARPA/NRaD Sensate Liner Workshop held Apr. 11, 1996; Author: Dr. Michael Burns, SME, Inc.

Slide Presentation Titled Personal Status Monitor from the DLA/ARPA/NRaD Sensate Liner Workshop held Apr. 11, 1996; Author: Lt. Gen. Peter Kind (Ret.), Sarcos.

Slide Presentation Titled Combat Casualty Care Overview from the DLA/ARPA/NRaD held Apr. 11, 1996; Author: Col. R. Satava ARPA.

Slide Presentation Titled Resources Available Through The Apparel Center At Southern Tech from the Sensate Liner Workshop held Apr. 11, 1996; Author: Dr. Larry Haddock, Southern Tech.

Slide Presentation Titled Introduction: Anthropology Research Project from the DLA/ARPA/NRaD Sensate Liner Workshop held Apr. 11, 1996; Author: Dr. Bruce Bradtmiller.

Slide Presentation Titled Applications For 3D Human Body Modelling from the DLA/ARPA/NRaD Sensate Liner Workshop held Apr. 11, 1996; Author: Dr. Robert M. Beecher, Beecher Research Company.

Slide Presentation Titled Prototype Development of Functional Clothing Research from the DLA/ARPA/NRaD Sensate Liner Workshop held Apr. 11, 1996; Author: Donna Albrecht, Univ. of Wisconsin.

Slide Presentation Titled An Overview of Clemson Apparel Research from the DLA/ARPA/NRaD Sensate Liner Workshop held Apr. 11, 1996; Author: Dr. Chris Jarvis, Clemson Apparel Research.

Slide Presentations from Proposal conference for the Sensate Liner For Combat Casualty Care Program dated Jun. 27, 1996.

Supplementary European Search Report of EP 00 94 7078.

* cited by examiner

| POF | PLASTIC OPTICAL FIBER |
|---|---|
| 560 SP | 560 DENIER POLYESTER/COTTON CORE-SPUN SPANDEX |
| P/C | 50/50 POLYESTER/COTTON BLENDED |

000# FABRIC OR GARMENT WITH INTEGRATED FLEXIBLE INFORMATION INFRASTRUCTURE FOR MONITORING VITAL SIGNS OF INFANTS

This application claims priority to U.S. provisional application No. 60/142,360, filed on Jul. 6, 1999, now abandoned, and is a continuation-in-part of U.S. Ser. No. 09/157,607, filed on Sep. 21, 1998, now U.S. Pat. No. 6,145,551, which claims priority to U.S. provisional application No. 60/059,444, filed on Sep. 22, 1997, now abandoned. This application is also a continuation-in-part of U.S. Ser. No. 09/273,175, filed on Mar. 19, 1999, now U.S. Pat. No. 6,381,482, which claims priority to U.S. provisional application No. 60/085,266, filed on May 13, 1998, now abandoned.

BACKGROUND OF THE INVENTION

1. Field of the Invention

The present invention relates to a fabric or garment, and which includes an integrated infrastructure for monitoring the vital signs of infants.

2. Background of the Art

Efforts have been made previously to create fabrics and garments which incorporate electrodes for monitoring the condition of the wearer, such as EKG, or conductive fibers for electromagnetic screening. For example, U.S. Pat. No. 4,668,545 to Lowe and U.S. Pat. No. 5,103,504 to Dordevic disclose fabrics including conductive fibers for electromagnetic screening and for protecting a wearer from magnetic radiation.

U.S. Pat. No. 4,580,572 to Granek et al. discloses a garment for delivering and receiving electric impulses which can include a conductive medium knitted or woven into the cloth, wires sewn onto the cloth or conducting cloth sewn onto nonconducting cloth.

However, these patents fail to disclose either a woven or knitted fabric which incorporates information infrastructure component in the form of a textile fiber which can include an electrical conductive component of the fabric for collecting or monitoring physical or vital signs of a wearer of the fabric and which may be worn and washed in the same manner as conventional clothing.

A need, therefore, exists for a fabric having an integrated information infrastructure which can be incorporated or fashioned into a wearable garment and which includes a flexible infrastructure for collecting, processing, transmitting and receiving information concerning a wearer of the garment. It is to the provision of such a fabric or garment with an integrated information infrastructure to which the present invention is one aspect directed.

A problem affecting infants is known as Sudden Infant Death Syndrome (SIDS). SIDS is generally the death of an infant, usually under one year old, that is unexplained by any prior medical diagnosis, postmortem examination or other factors. SIDS is the leading cause of post-neonatal mortality in the United States, accounting for almost 40% of deaths in infants from 1 month to 1 year of age. Approximately 7 of every 10,000 live born infants in the United States succumb to SIDS. Infants that are classified to have a higher risk of the likelihood of SIDS include premature infants, siblings of SIDS victims and infants who have experienced apparent life-threatening episodes, e.g., turning blue and/or stoppage of respiration.

To detect problems that can lead to SIDS, special home cardiorespiratory monitors can be used to receive data about the infant. The data is obtained at the infant's home by a home cardiorespiratory monitor that is attached to the infant and records the infant's heart rate and chest wall movement. The heart rate and breathing rate can be monitored by simple cardiorespiratory sensors (e.g., EKG) attached to the infant. The monitor continuously records data about the infant's heart rate and breathing. If certain preset parameters for apnea and/or bradycardia are violated, the monitor sets out an alarm to warn the caregiver of the problem and the monitor will record the EKG, trend event of the heart rate and the respiratory waveform. The recorded data can be downloaded by telephone modem to a specialized apnea center at a hospital in order to verify the event. The data can then be utilized by specialist physicians who receive the data from the monitors to diagnose the cause of the episode that caused the breathing or heart to stop or slow to abnormal levels. The potential problems include heart blocks, arrhythmias, and seizures which are difficult for a primary care physician to detect.

A problem with home cardiorespiratory monitors is that even when available they are not used. There are three major causes for the non-use of the cardiorespiratory monitors. First, is that most of the electrodes used to record the vital signs are rubberized electrode patches that are placed on the infant's chest and are held in place by VELCRO belts applied over the patches. These VELCRO belts are difficult to apply. If not applied properly, the belt and/or electrodes irritate the infant's skin (sometimes to the point of blistering and even bleeding). Second, they can also trigger false alarms. For these reasons, the parents may stop using the equipment. Lastly, caregivers and parents are reluctant to use the monitor because they believe that the protruding wires that go from the sensors on the body to the monitoring equipment can wrap around the neck of the infant if the infant rolls over.

Therefore, there exists a need for a device that overcomes the problems with using VELCRO belts to hold the sensors in place on the infants for monitoring them using cardiorespiratory monitors to prevent SIDS.

It is to the provision of such a fabric or garment to meet the two needs to which the present invention is one aspect directed.

SUMMARY OF THE INVENTION

In one embodiment, the present invention comprises a garment for infants comprising a comfort component serving as a base, a plurality of signal transmission paths integrated within the comfort component, and at least one interface that provides a transmission path between the information infrastructure component that is part of the garment and the external device.

In another embodiment, the present invention comprises a garment for infants comprising a comfort component serving as a base, a form-fitting component to provide a 'form fit' to the wearer, a plurality of signal transmission paths integrated within the comfort component and at least one interface that provides a transmission path between the information infrastructure component that is part of the garment and the external device. In additional embodiments, this garment may be made up of an additional static dissipating component and with or without the form-fitting component (the comfort component and plurality of signal paths will be required).

In another embodiment, the present invention comprises a fabric comprising a comfort component, an information infrastructure component integrated within the comfort component, and at least one interface that provides a transmission path between the information infrastructure component and an external device.

In any of the above embodiments, the garments can further comprise means for adjusting the size of the garment, means for easily attaching and detaching sensors and means for easily putting on and taking off the garment.

DETAILED DESCRIPTION OF THE ILLUSTRATIVE EMBODIMENTS

Figure 1:
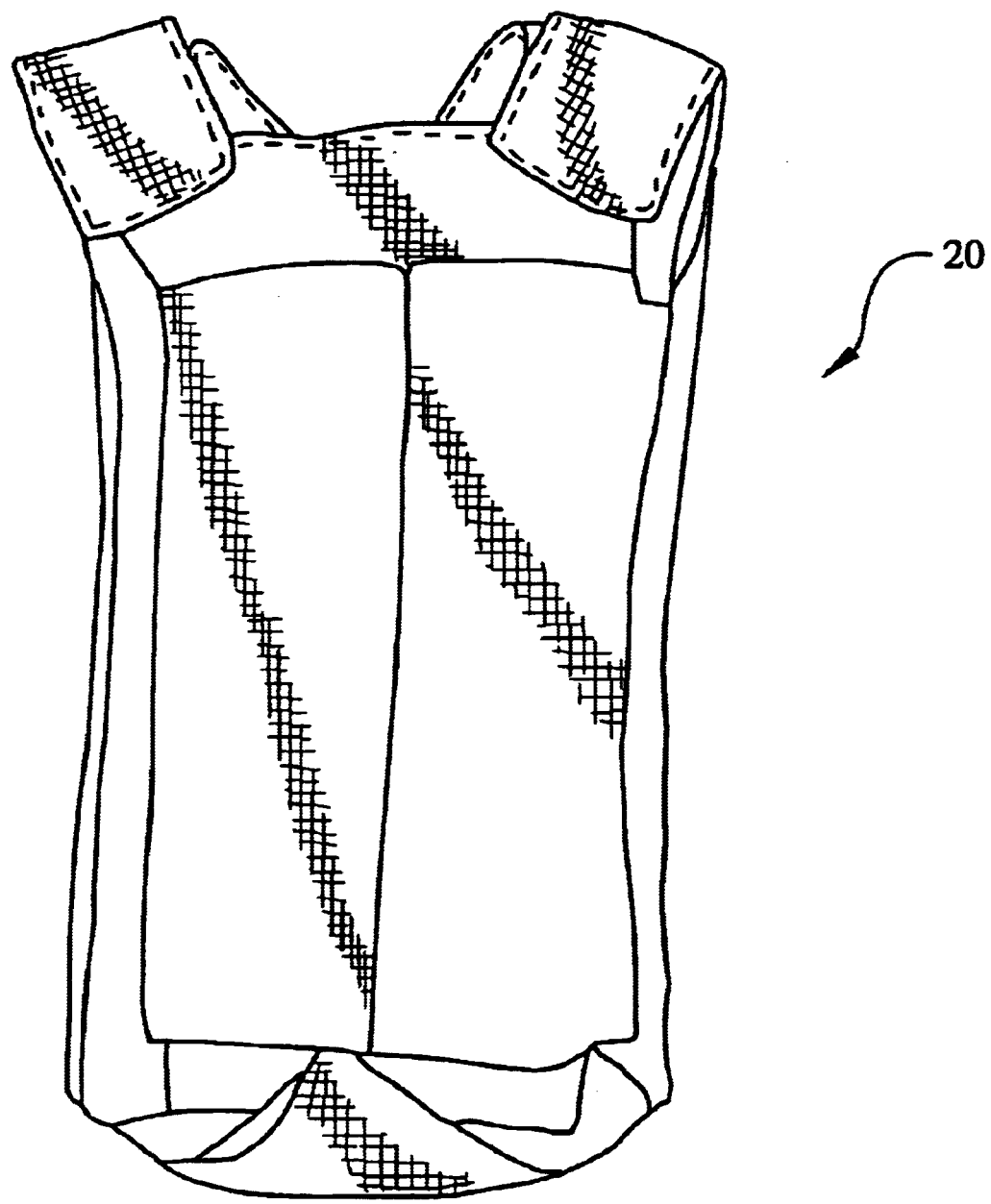
FIG. 1 is a front elevational view of a garment into which the wearable fabric with integrated information infrastructure of the present invention has been incorporated.

Referring now to the above figures, wherein like reference numerals represent like parts throughout the several views, the fabric of the present invention having a multi-functional information infrastructure integrated within the fabric for information collection, processing, reception and transmission capability, along with capability to easily wear and adjust the size of the garment will be described in detail.

The fabric of our present invention is wearable and, thus, provides a wearable information infrastructure integrated within the fabric that has hitherto been typically resident in a computer. When fitted with, or connected to, a data collector(s) such as, but not limited to, a sensor for monitoring body physical signs and connected to a data transmitter or processing unit, as described in detail below, our wearable fabric provides information pathways that allow the sensor to provide information to the transmitter or processor, and vice versa. In this context, the information infrastructure of our fabric invention can manage the transfer of data between the sensor and the transmitter or processing unit. Since the sensor can be considered a "hardware peripheral", our wearable fabric, which can be fashioned into a garment, having an integrated information infrastructure can be conceived of as a "wearable motherboard." When we use the term "wearable motherboard", we are using the term in the context described immediately above.

A. A Fabric Having An Integrated Flexible Information Infrastructure in Accordance With the Present Invention As illustrated generally in FIG. 1, the fabric of our present invention can be integrated or fashioned into a garment, for example an undershirt, by any appropriate joining technique, such as by sewing, gluing, attachment through a hook and loop-type fastener, such as VELCRO, buttons, zipper, and the like. The fabric provides an infrastructure for a garment for collecting, monitoring, and/or tracking data regarding physical conditions of a wearer of the garment, such as body vital signs or voice, and transmitting such data to a remote location. The fabric can be provided with means in the form of sensors, or connectors for sensors to be worn on the body, for monitoring body physical signs, such as heart rate or EKG, pulse, voice and temperature, and blood oxygen levels, and atmospheric exposure, such as chemical and biological exposure, atmospheric smoke and oxygen levels, radiation exposure, as well as penetration. The fabric with integrated information infrastructure consists of the following components: a base fabric or "comfort component," and an information infrastructure component. The base fabric can be either a two-dimensional woven or knitted fabric into which the information infrastructure component is incorporated. Additionally, either or both a form-fitting component and a static dissipating component may be included, if desired. Finally, it can be a tubular, woven or knitted fabric or a full-fashioned garment with the integrated information infrastructure component.

The information infrastructure component can include any or all of the following, individually or in any combination, electrically conductive components, sensors, processors, or wireless transmission devices and, if desired, penetration detection components.

1. Knitted Fabric

Figure 4:
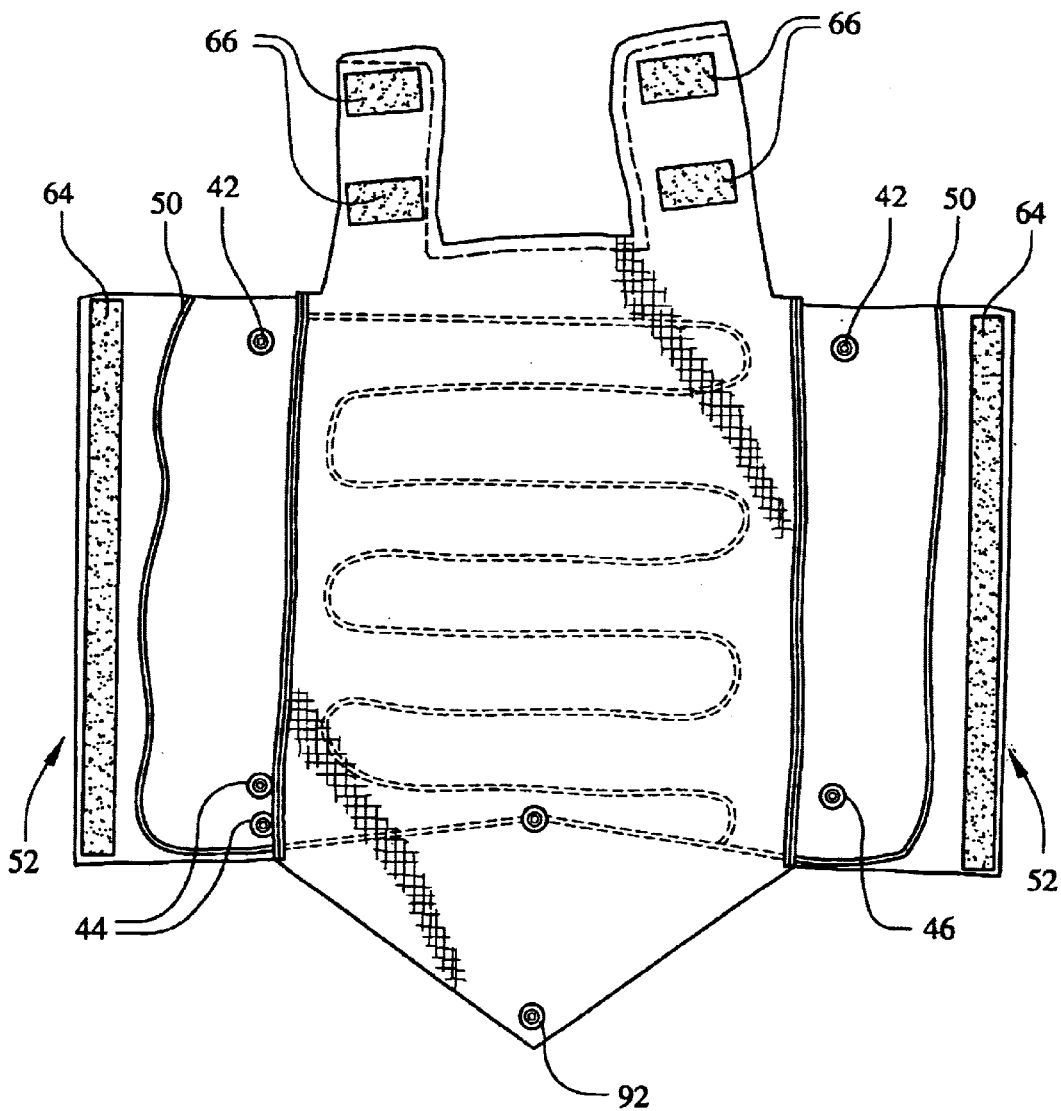
FIG. 4 is the inside view of the back panel (piece) of the garment of the present invention with the signal transmission paths, the T-Connectors for the connecting wires (sensor leads) and the means for adjusting the garment size and binding to the front panel of the garment.

FIG. 1 illustrates one embodiment of the fabric (garment) of the present invention consisting of a knitted comfort component of cotton yarn. A data bus for carrying the sensor data or other information is integrated into the fabric in two ways: (i) by inlaying the conducting yarn 25 in the structure (FIG. 2); and (ii) by knitting the conducting fibers as a "bus" 50 separately and attaching it to the sides of the fabric as flaps 52 (FIG. 4). The garment is made up of two parts or panels: the front part shown in FIG. 2 and the back part shown in FIG. 4. The two parts or panels are bound together by means of VELCRO 60, 64 to provide the right degree of form and fit so that the garment is comfortable for the baby while providing the required functionality. Although VELCRO is preferred, other joining means such as sewing, gluing, hooks, zippers and buttons or any combination thereof can be used to integrate the two parts.

Figure 2:
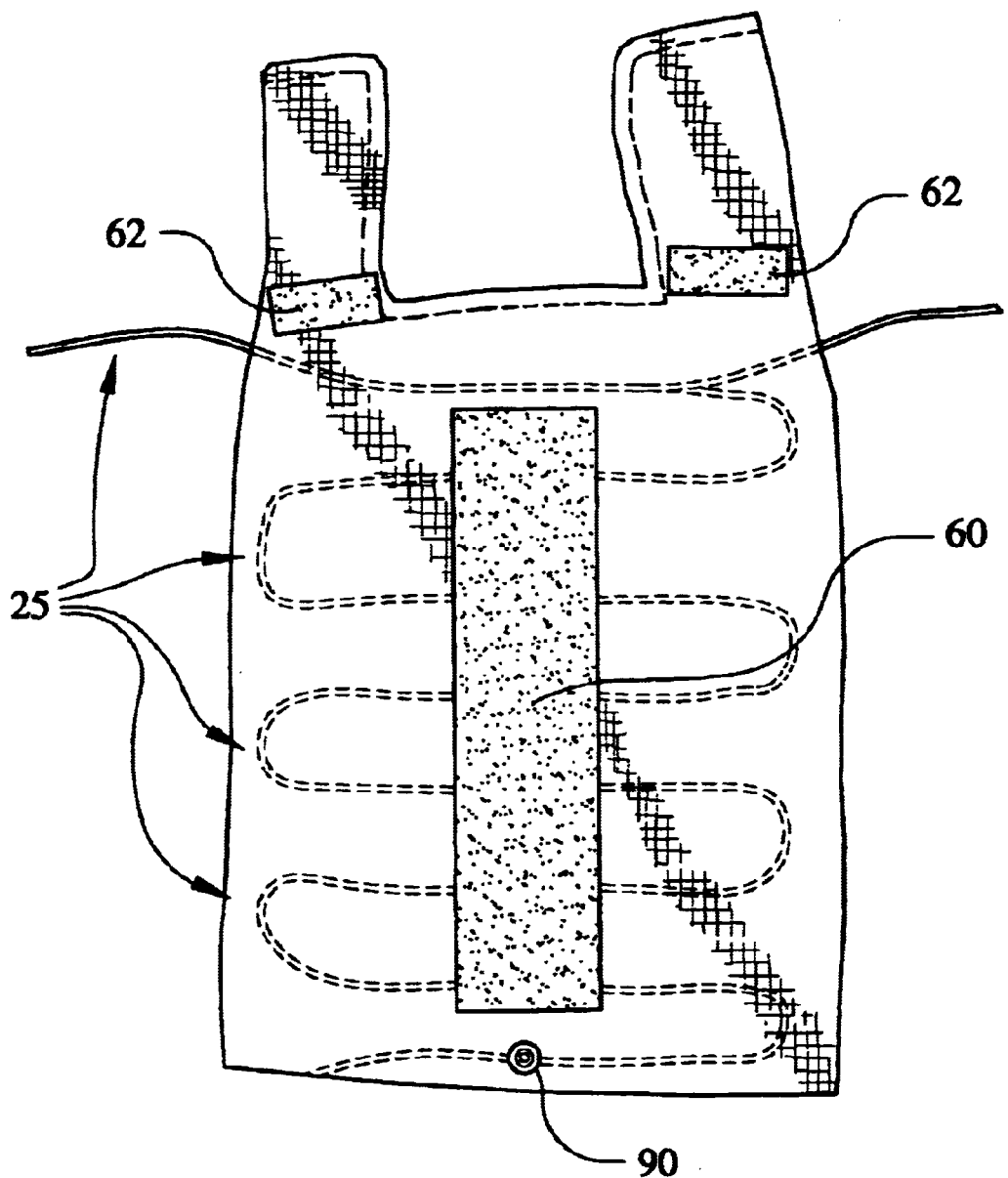
FIG. 2 is the outside view of the front panel (piece) of the garment of the invention in which the means for adjusting the size of the garment are shown along with the signal transmission paths.

FIG. 2 shows the VELCRO strip 60 in the center of the outside of the front panel (piece) of the garment into which the VELCRO strips 64 on the flaps 52 of the back panel (piece) will join to provide the correct fit to the infant. Thus, the garment of the present invention can be adjusted in size (using the adjustable VELCRO strips) to accommodate the baby's growth. The VELCRO strips 62 in the front piece and 66 in the back piece provide the capability to adjust the shoulder size to better fit the baby. The front and back pieces can be joined at the bottom using the closures 90 and 92 in FIGS. 2 and 4, respectively, thus creating the complete well-fitting garment shown in FIG. 1.

| Parameter | Details |
| --- | --- |
| Knitting Machine | Flat Bed |
| Description | 1x1 Rib |
| Gauge (Needles Per Inch) | 5 |
| Width | 10 Inches |
| Wales per Inch | 10 |
| Courses per Inch | 20 |
| Comfort Component: Cotton | 16s Ne Yarn |
| Electrical Conductive Components | X-Static Conducting Nylon fiber with insulated PVC Sheath from Sauquoit Industries, Pennsylvania |

Figure 3:
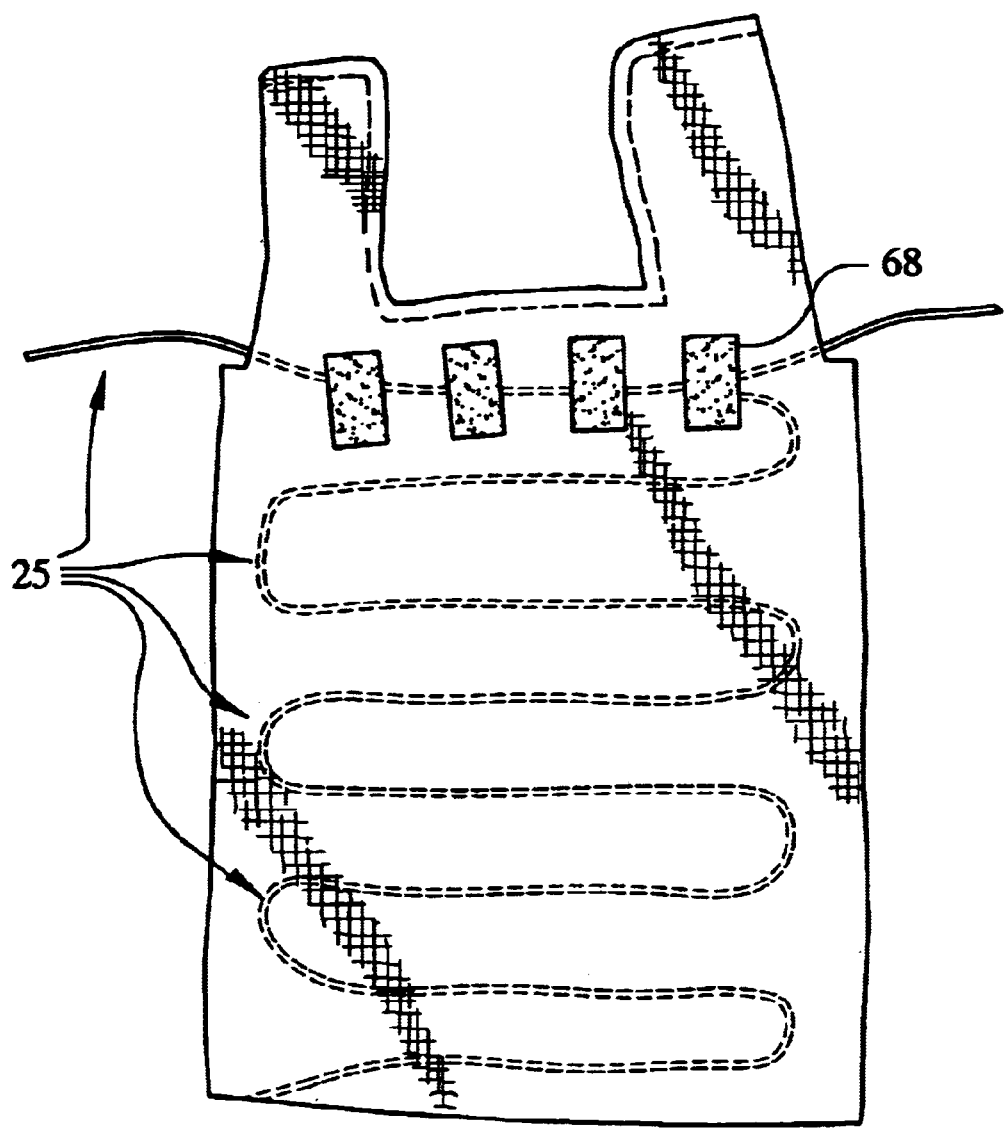
FIG. 3 is the inside view of the front panel of the garment of the invention in which the means for attaching the sensors are shown along with the signal transmission paths.
Figure 5:
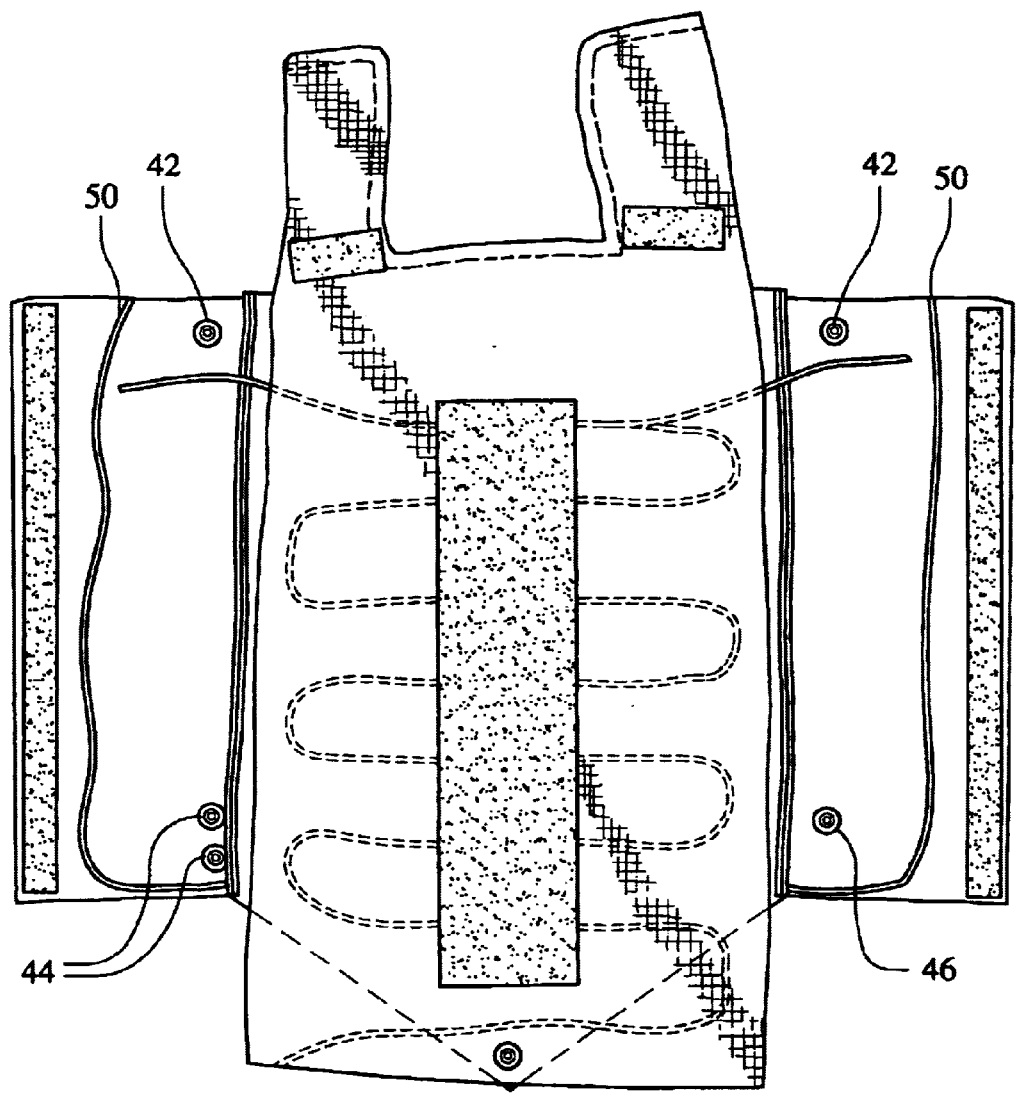
FIG. 5 shows the opened out view with the two panels (front and back) of the garment of the present invention overlaid on top of each other.
Figure 6:
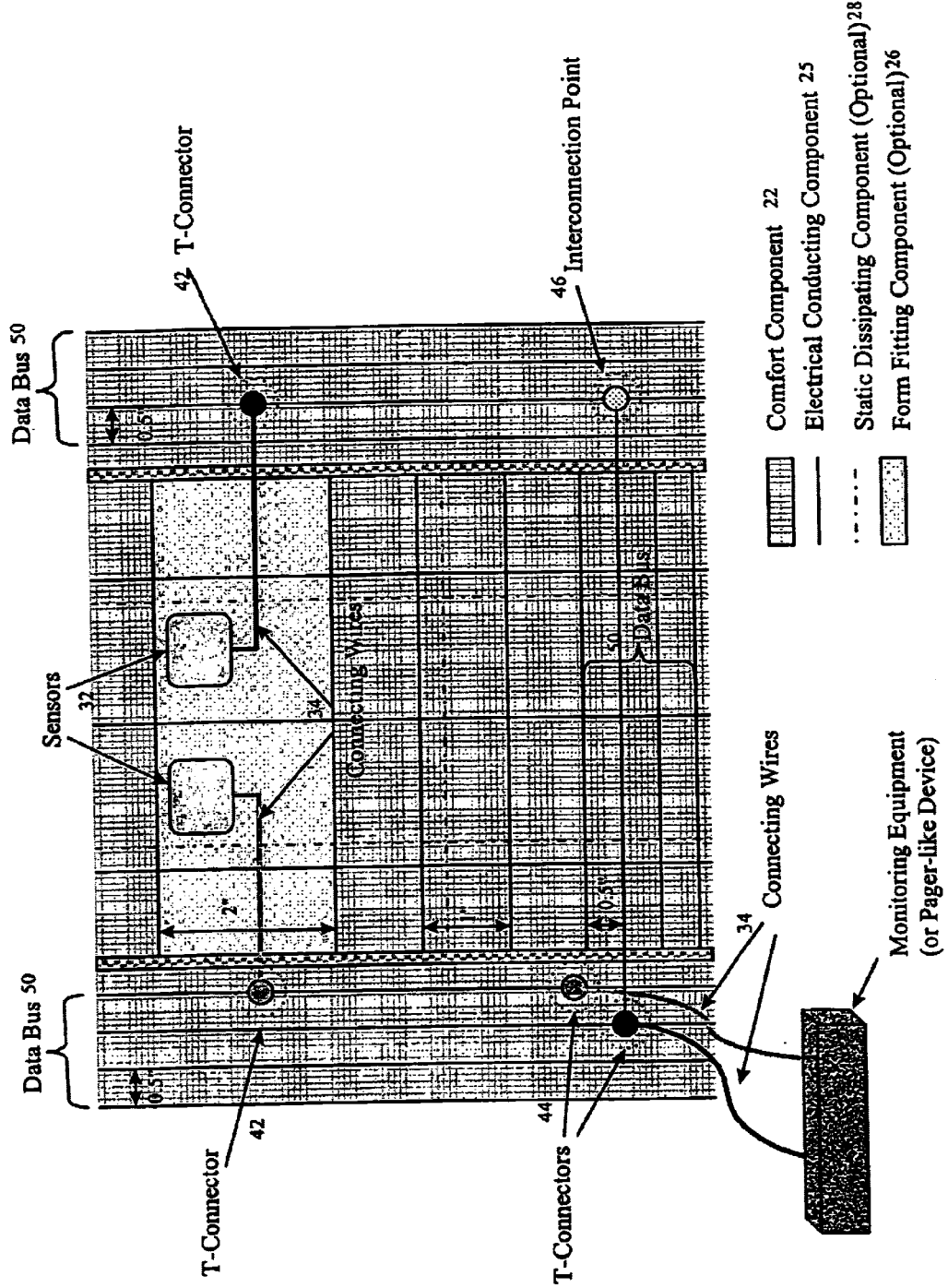
FIG. 6 shows the schematic layout or overall architecture of one embodiment of the garment of the present invention in FIG. 1.

The above table shows the parameters used for producing the knitted fabric embodiment of our present invention having an information infrastructure integrated within the fabric as shown in FIG. 5. These parameters can be adjusted, as desired, to affect the characteristics of the resulting knitted fabric. The comfort component, Cotton 22 forms the 1x1 rib structure and serves as the base of the fabric. The Electrical Conductive Yarn 25 is inlaid in the structure as shown in FIGS. 2–4. The electrical bus 50 in the structure is also shown in FIGS. 4 and 5. In this embodiment, the electrical bus 50 has been knitted separately and attached to the structure. The schematic layout of the garment of one embodiment of the present invention is shown in FIG. 6.

The comfort component 22 is the base of the fabric and can in one embodiment be a standard fabric used as component of clothing. The comfort component will ordinarily be in immediate contact with the wearer's skin and will provide the necessary comfort properties for the fabric/garment. Therefore, the chosen material should preferably provide at least the same level of comfort and fit as compared to a typical fabric used for clothing, e.g., good fabric hand, air permeability, moisture absorption and stretchability.

The comfort component can consist of any yarn applicable to conventional apparel fabrics. The choice of material for the yarn will ordinarily be determined by the end use of the fabric and will be based on a review of the comfort, fit, fabric hand, air permeability, moisture absorption and structural characteristics of the yarn. Suitable yarns include, but are not limited to, cotton, polyester/cotton blends and microdenier polyester/cotton blends.

The fibers preferably suitable for use in the comfort component are cotton, polyester, and microdenier polyester/cotton blend. Cotton is a natural fiber and possesses excellent moisture absorption properties and is very soft on the skin. It has the required mechanical and abrasion properties and is typically used for undergarments; it is especially desirable for baby clothes. Microdenier polyester/cotton blends are extremely versatile fibers and are characterized by: (a) good feel, i.e., handle; (b) good moisture absorption; (c) good mechanical properties and abrasion resistance; and (d) ease of processing. It should be recognized that other fibers meeting such performance requirements are also suitable. Microdenier polyester/cotton blended fibers are available from Hamby Textile Research of North Carolina. Microdenier fibers for use in the blend are available from DuPont.

The information infrastructure component of the fabric 20 can include materials 25 for sensing one or more body vital signs. These materials are inlaid during the knitting of the comfort component of the fabric. They can also be knitted separately, as a bus 50 and attached to the fabric as shown in FIG. 4. After fashioning of the fabric into a garment is completed, these materials can be connected to a monitor (referred to as a "personal status monitor" or "PSM") which will take readings from the sensing materials, monitor the readings and issue an alert depending upon the readings and desired settings for the monitor, as described in more detail below. The PSM can also be used for geolocations (GPS, and a spread spectrum ratio) of its wearer. One example of the PSM is the cardiorespiratory monitoring unit from Respironics, Inc. which is commonly used for monitoring infants prone to SIDS. Alternatively, the PSM can be a 'pager-like' device that can transmit the information through wireless technology and eliminate the "physical" hook-up (using connecting wires 34) of the monitoring equipment to the garment of the present invention.

The information infrastructure component may consist of either a high or a low conductivity electrical conducting material component (ECC) 25 or both high and low conductivity fibers. The electrical conductive fiber preferably has a resistivity of from about $0.07 \times 10^{-3}$ to 10 kohms/cm. The ECC 25 can be used to monitor one or more body vital signs including heart rate, pulse rate, temperature, and oxygen saturation (pulse ox), through sensors on the body and for linking to a personal status monitor (PSM). It can also be used to monitor levels of selected parameters in the body's environment, such as chemical, biological, and radiation (nuclear) levels, as well as smoke levels and oxygen content in the atmosphere. Suitable materials include the three classes of intrinsically conducting polymers, doped fibers and metallic fibers, respectively.

Polymers that conduct electric currents without the addition of conductive (inorganic) substances are known as "intrinsically conductive polymers" (ICP). Electrically conducting polymers have a conjugated structure, i.e., alternating single and double bonds between the carbon atoms of the main chain. In the late 1970s, it was discovered that polyacetylene could be prepared in a form with a high electrical conductivity, and that the conductivity could be further increased by chemical oxidation. Thereafter, many other polymers with a conjugated (alternating single and double bonds) carbon main chain have shown the same behavior., e.g., polythiophene and polypyrrole. Initially, it was believed that the processability of traditional polymers and the discovered electrical conductivity could be combined. However, it has been found that the conductive polymers are rather unstable in air, have poor mechanical properties and cannot be easily processed. Also, all intrinsically conductive polymers are insoluble in solvents and they possess a very high melting point and exhibit little other softening behavior. Consequently, they cannot be processed in the same way as normal thermoplastic polymers and are usually processed using a variety of dispersion methods. Because of these shortcomings, fibers made up of fully conducting polymers with good mechanical properties are not yet commercially available and hence are not presently preferred for use in the fabric.

Yet another class of conducting fibers consists of those that are doped within organic or metallic particles. The conductivity of these fibers is quite high if they are sufficiently doped with metal particles, but this would make the fibers less flexible. Such fibers can be used to carry information from the sensors to the monitoring unit if they are properly insulated.

Metallic fibers, such as copper and stainless steel insulated with polyethylene or polyvinyl chloride, can also be used as the conducting fibers in the fabric. With their exceptional current carrying capacity, copper and stainless steel are more efficient than any doped polymeric fibers. Also, metallic fibers are strong and they resist stretching, neck-down, creep, nicks and breaks very well. Therefore, metallic fibers of very small diameter (of the order of 0.1 mm) will be sufficient to carry information from the sensors to the monitoring unit. Even with insulation, the fiber diameter will be less that 0.3 mm and hence these fibers will be very flexible and can be easily incorporated into the fabric. Also, the installation and connection of metallic fibers to the PSM unit will be simple and there will be no need for special connectors, tools, compounds and procedures. One example of a high conductive yarn suitable for this purpose is Bekinox available from Bekaert Corporation, Marietta, Ga., a subsidiary of Bekintex NV, Wetteren, Belgium, which is made up of stainless steel fibers and has a resistivity of 60 ohm-meter. The bending rigidity of this yarn is comparable to that of the polyamide high-resistance yarns and can be easily incorporated into the information infrastructure in our present invention.

Thus, the preferred electrical conducting materials for the information infrastructure component for the fabric are: (i) doped nylon fibers with conductive inorganic particles and insulated with PVC sheath; (ii) insulated stainless steel fibers; and (iii) thin gauge copper wires with polyethylene sheath. All of these fibers can readily be incorporated into the fabric and can serve as elements of a wearable motherboard, described below. An example of an available conducting fiber is X-Static coated nylon with PVC insulation (T66) from Sauquoit Industries, Scranton, Pa. An example of an available thin copper wire is 24-gauge insulated copper wire from Ack Electronics, Atlanta, Ga.

The electrical conducting component fibers 25 can be incorporated into the knitted fabric in two ways: (a) regularly spaced inlaid yarns acting as sensing elements; and (b) precisely positioned (inlaid) yarns for carrying signals from the sensors to the PSM. Additionally, the yarns can be knitted separately into a comfort component and the data bus 50 can be attached to the fabric as shown in FIGS. 4 and 6.

The form-fitting component (FFC) 26 provides form-fit to the wearer, if desired. More importantly, it keeps the sensors in place on the wearer's body during movement. Therefore, the material chosen should have a high degree of stretch to provide the required form-fit and at the same time, be compatible with the material chosen for the other components of the fabric. Any fiber meeting these requirements is suitable. The preferred form-fitting component is SPANDEX fiber, a block polymer with urethane groups. Its elongation at break ranges from 500 to 600% and, thus, can provide the necessary form-fit to the garment. Its elastic recovery is also extremely high (99% recovery from 25% stretch) and its strength is in the 0.6–0.9 grams/denier range. It is resistant to chemicals and withstands repeated machine washings and the action of perspiration. It is available in a range of linear densities.

The SPANDEX band 26 shown in FIG. 6 is the FFC providing the desired form-fit. These bands behave like "straps", but are unobtrusive and are well integrated into the fabric. There is no need for the wearer to tie something to ensure a good fit for the garment. Moreover, the SPANDEX band will expand and contract as the wearer's chest expands and contracts during normal breathing. The FFC may not be always be necessary especially for the knitted versions of the fabric/garment.

The purpose of the static dissipating component (SDC) 28 is to quickly dissipate any built-up static charge during the usage of the fabric. Such a component may not always be necessary. However, under certain conditions, several thousand volts may be generated which could damage the sensitive electronic components in the PSM Unit. Therefore, the material chosen must provide adequate electrostatic discharge protection (ESD) in the fabric.

NEGA-STAT, a bicomponent fiber produced by DuPont is the preferred material for the static dissipating component (SDC). It has a trilobal shaped conductive core that is sheathed by either polyester or nylon. This unique trilobal conductive core neutralizes the surface charge on the base material by induction and dissipates the charge by air ionization and conduction. The nonconductive polyester or nylon surface of NEGA-STAT fiber controls the release of surface charges from the thread to provide effective static control of material in the grounded or ungrounded applications according to specific end-use requirements. The outer shell of polyester or nylon ensures effective wear-life performance with high wash and wear durability and protection against acid and radiation. Other materials which can effectively dissipate the static charge and yet function as a component of a wearable, washable garment may also be used.

Figure 7:
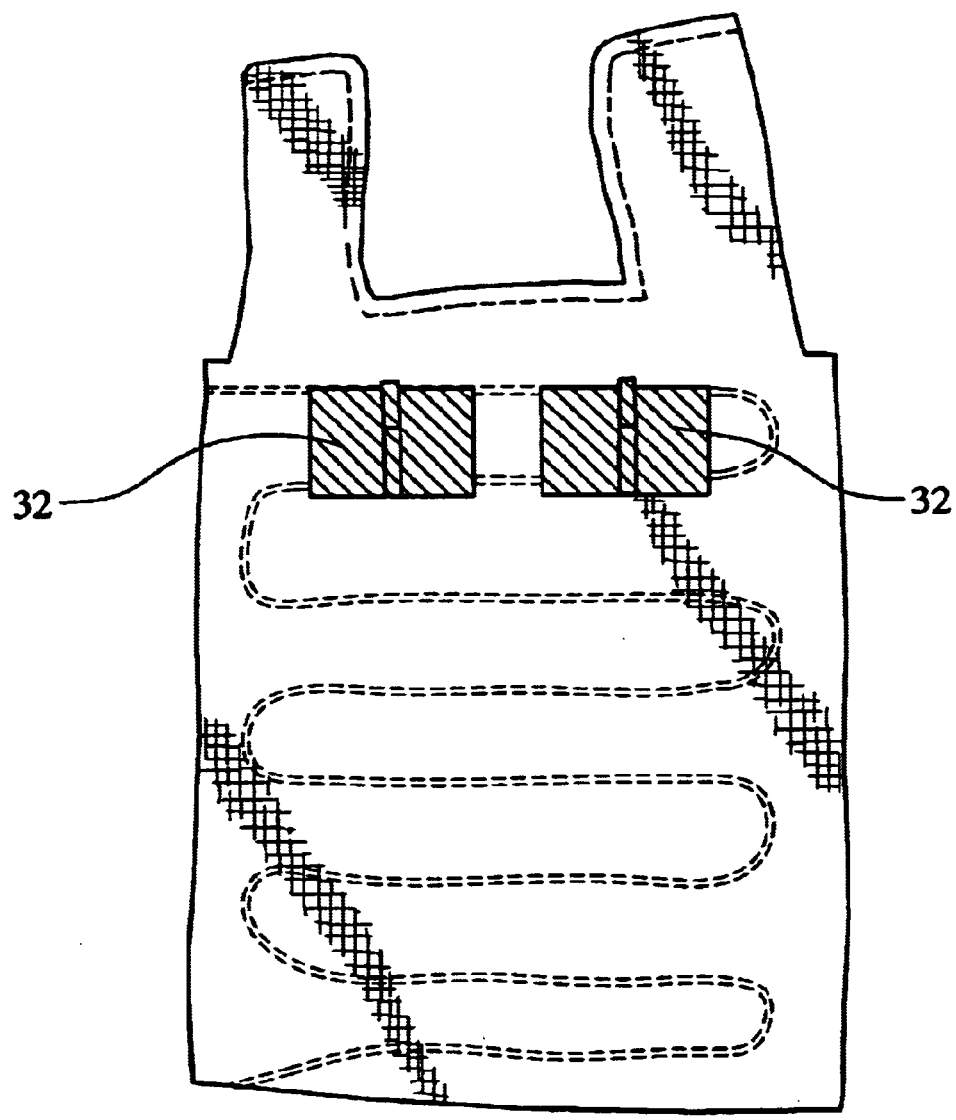
FIG. 7 is the view with the sensors attached to the inside of the front piece (FIG. 3) of the garment of the present invention.
Figure 8:
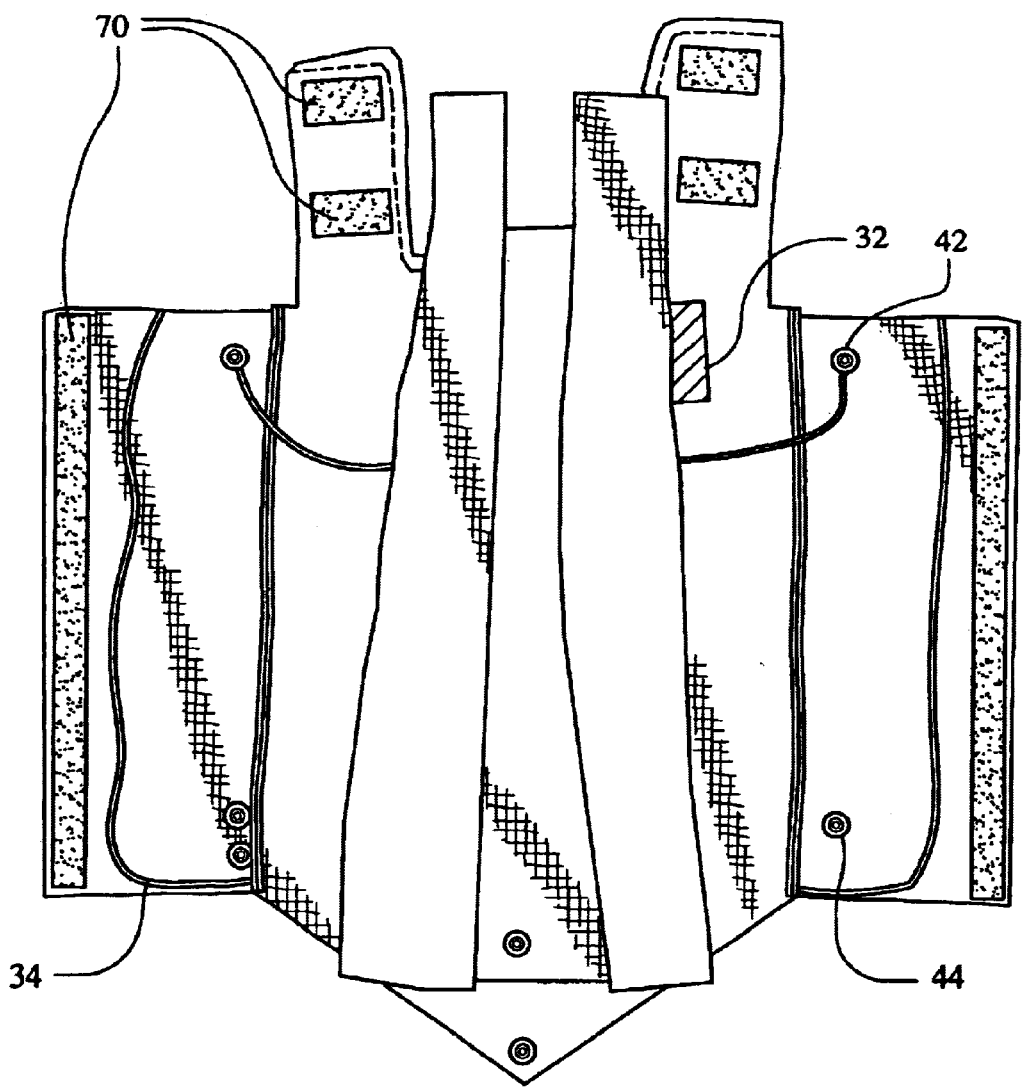
FIG. 8 is the view with the sensor leads or connecting wires plugged into the top set of T-Connectors in FIG. 4.
Figure 9:
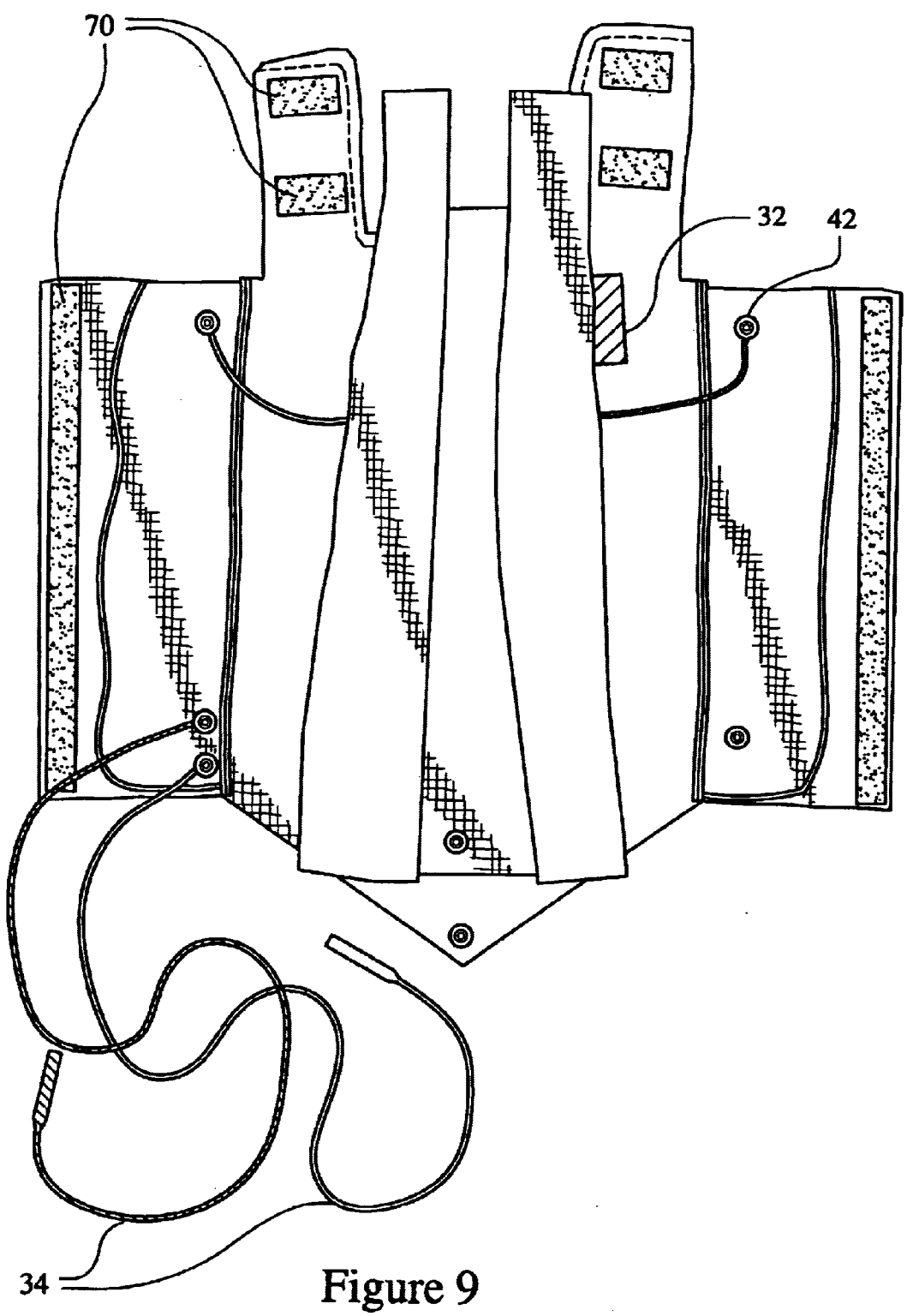
FIG. 9 is the view with the connecting wires carrying the vital signs data to the monitoring equipment plugged into the bottom set of T-Connectors in FIG. 4.

With reference to FIG. 3, the VELCRO strips 68 can be used to connect the body sensors 32 to the inside of the front piece of the garment of the present invention. This is illustrated in FIG. 7 which shows the sensors 32 attached to the front piece. The connecting wires from the sensors can be plugged into the top set of T-Connectors (similar to the "button clips" used in clothing), of the back panel of the garment shown in FIG. 5. This is illustrated in FIG. 8 where the connecting wires 34 are plugged into the top set of T-Connectors 42. The vital signs gathered by the sensors pass through the connecting wires or sensor leads 34 into the T-Connectors (42) at the top and are transmitted through the electrical conducting component 25 and the data bus 50 integrated into the garment (FIG. 5). This information is tapped out to the monitoring equipment or PSM through another set of connecting wires 34 plugged into the bottom set of T-Connectors 44. This is illustrated in FIG. 9. The schematic in FIG. 6 also clearly illustrates the data path in one embodiment of the garment of the present invention.

Figure 15:
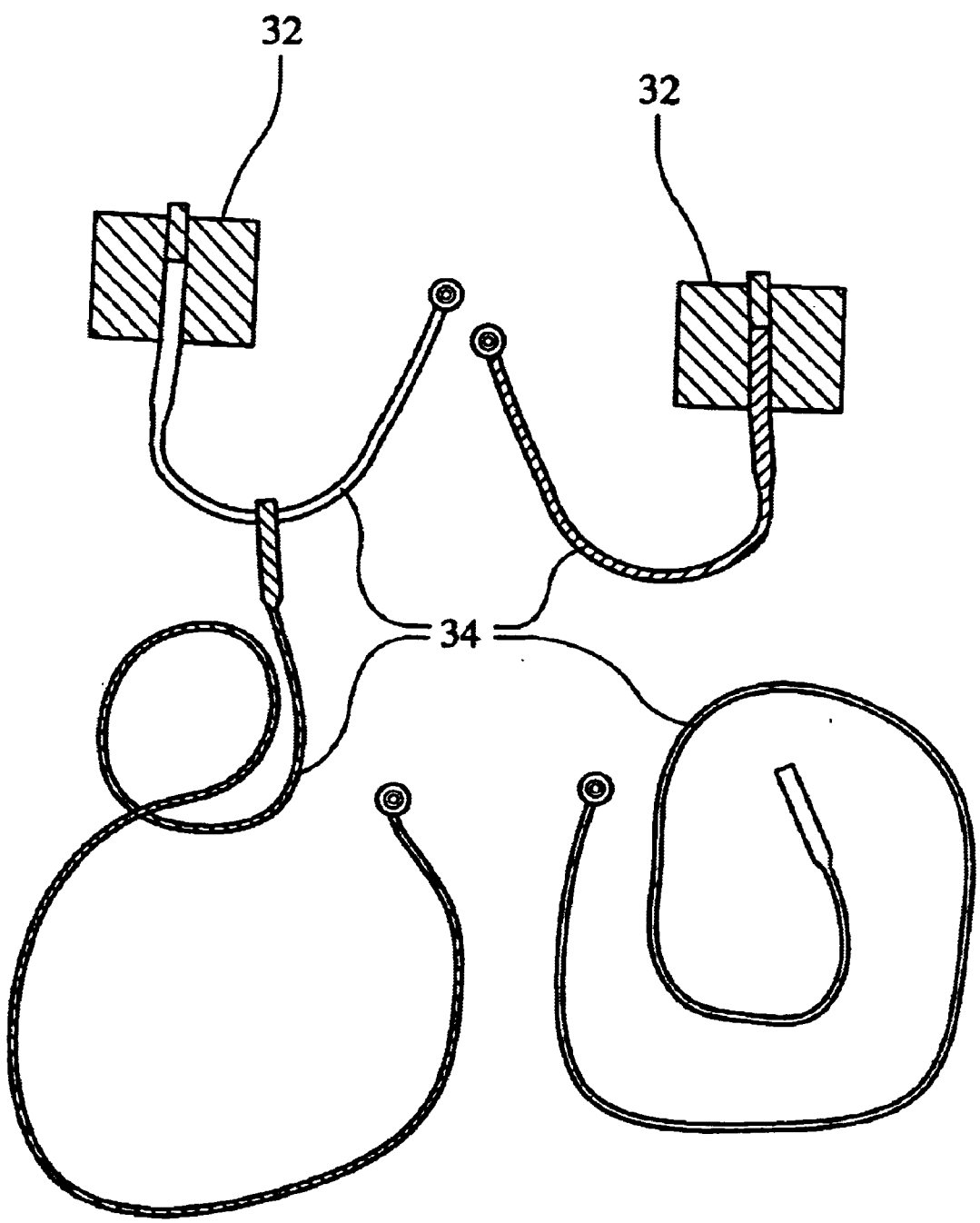
FIG. 15 shows the sensors and the sensor leads (connecting wires) that are used to plug into the T-Connectors integrated into the garments of the present invention.

By modularizing the design of the fabric 20 (using these VELCRO strips 68 and T-Connectors 42, 44), the sensors 32 and the connecting wires 34 themselves (shown in FIG. 15) can be made independent of the fabric 20. This accommodates different body shapes. The connector makes it relatively easy to attach the sensors to the wires. Yet another advantage of separating the sensors themselves from the garment, is that they need not be subjected to laundering when the garment is laundered, thereby minimizing any damage to them. However, it should be recognized that certain types of sensors such as RespiTrace™ can be knitted directly into the structure. Also, instead of, or in addition to, the VELCRO strips 68, T-Connectors can be used on the front piece to accommodate certain types of sensors (e.g., those used for EKG in hospitals).

The specifications for the preferred materials to be used in the production of our fabric/garment are as follows:

| Component | Materials | Count (CC) |
|---|---|---|
| Comfort (CC) | Cotton Microdenier Poly/Cotton Blend | 18s Ne |
| Form-fitting (FFC) | SPANDEX | 6s Ne Core-Spun from 560 denier SPANDEX yarn |
| Global and Random Electrical Conducting (ECC) | X-static Nylon with PVC Insulation Stainless Steel with PVC Insulation | 6s Ne 110 Tex |
| Static Dissipating (SDC) | NEGA-STAT | 18s Ne |

The yarn counts have been chosen based on initial experimentation using yarn sizes that are typically used in undergarments. Other yarn counts can be used. The weight of the fabric is around 6 oz/yd$^2$ or less.

Figure 11:
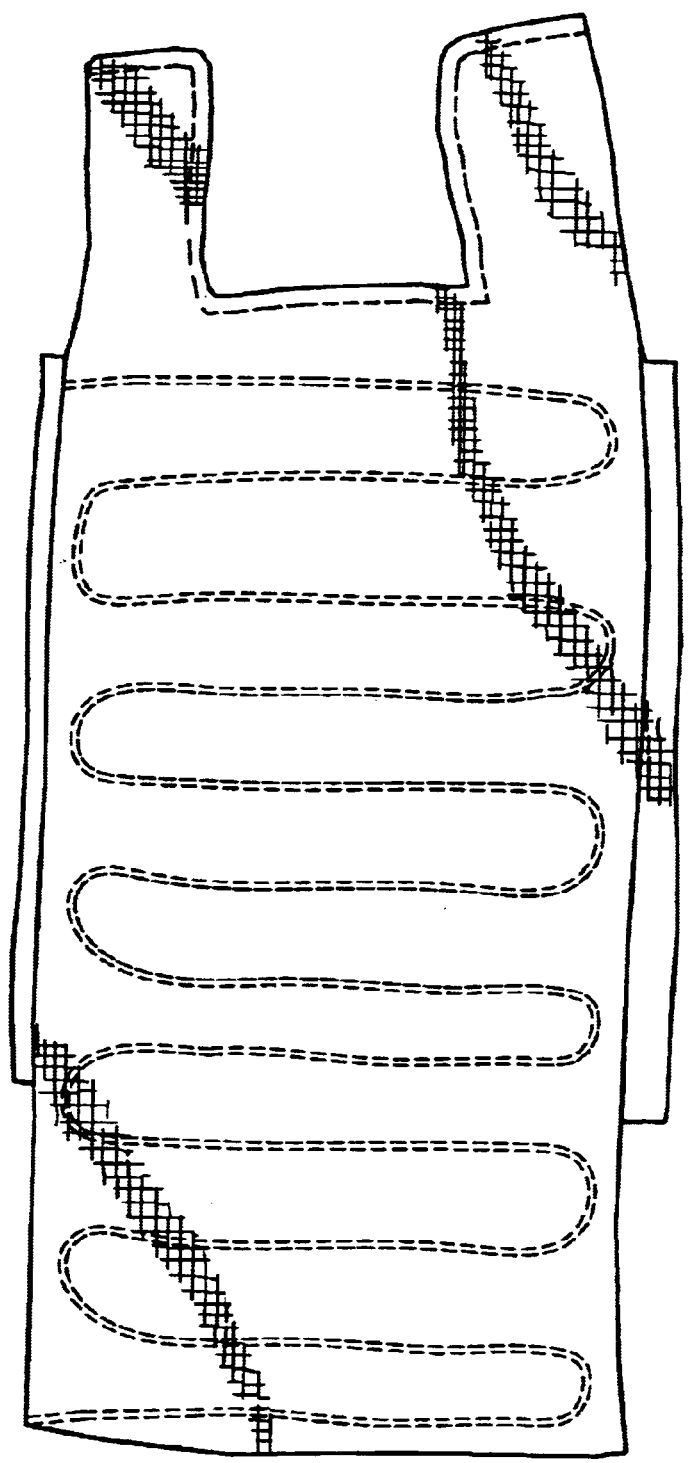
FIG. 11 illustrates another embodiment of the present invention.
Figure 12:
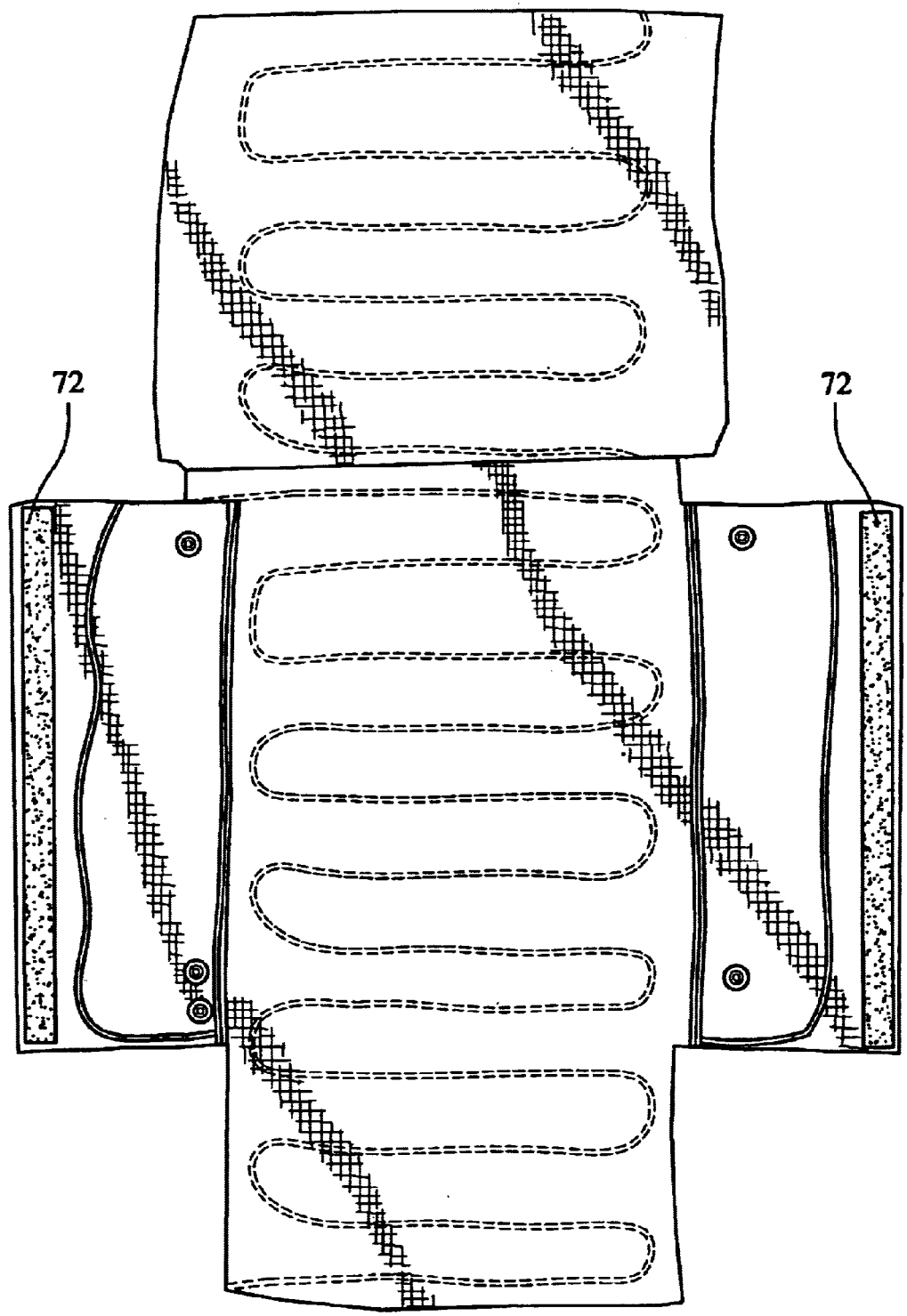
FIG. 12 illustrates the opened out view of FIG. 11 in which the T-connectors have been connected to electrically conductive fibers using the interconnection technology of FIG. 10.
Figure 13:
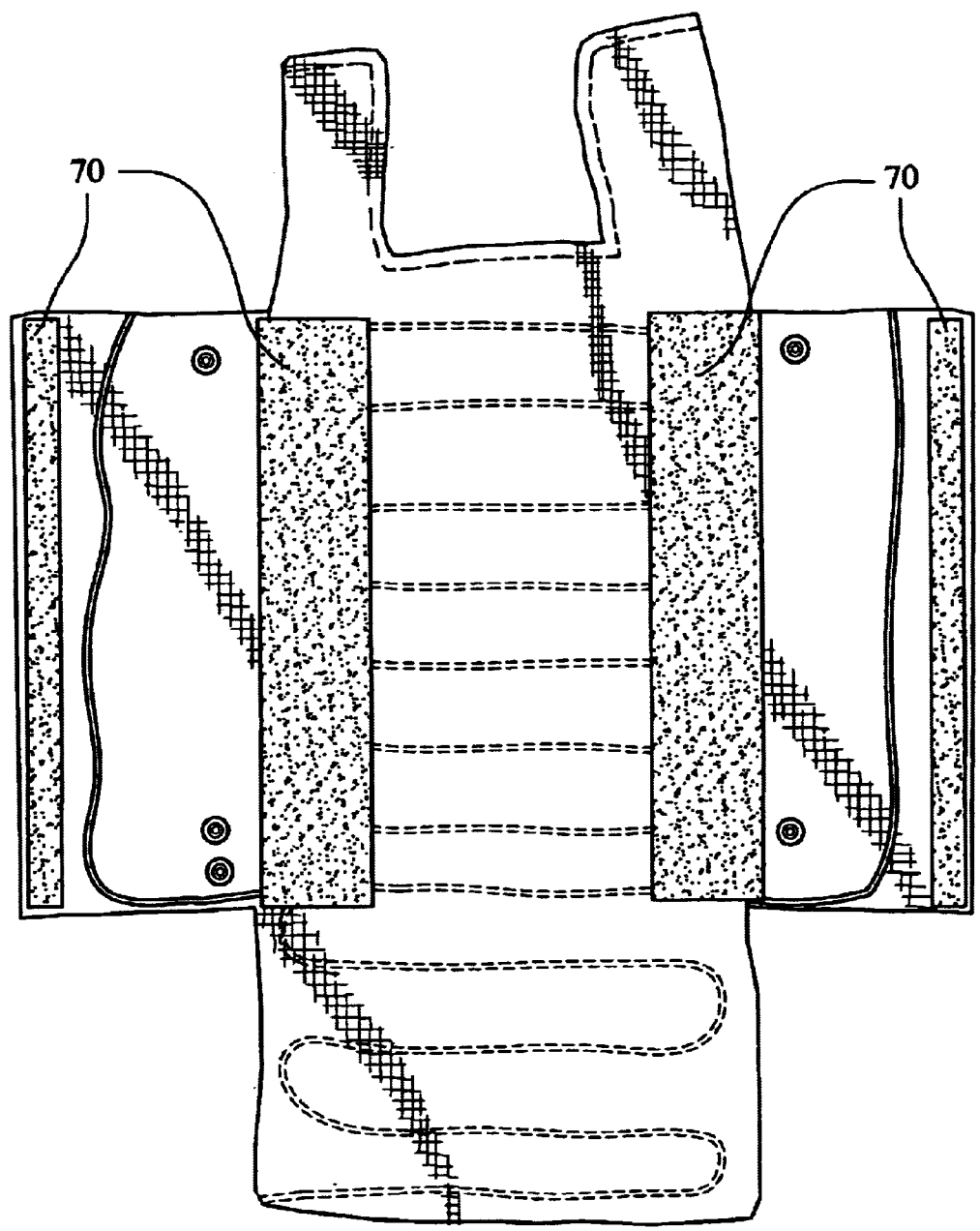
FIG. 13 is the rear view of the embodiment in FIG. 11 showing the VELCRO attachments on the back side of the garment and the flaps on the front side of the garment.
Figure 14:
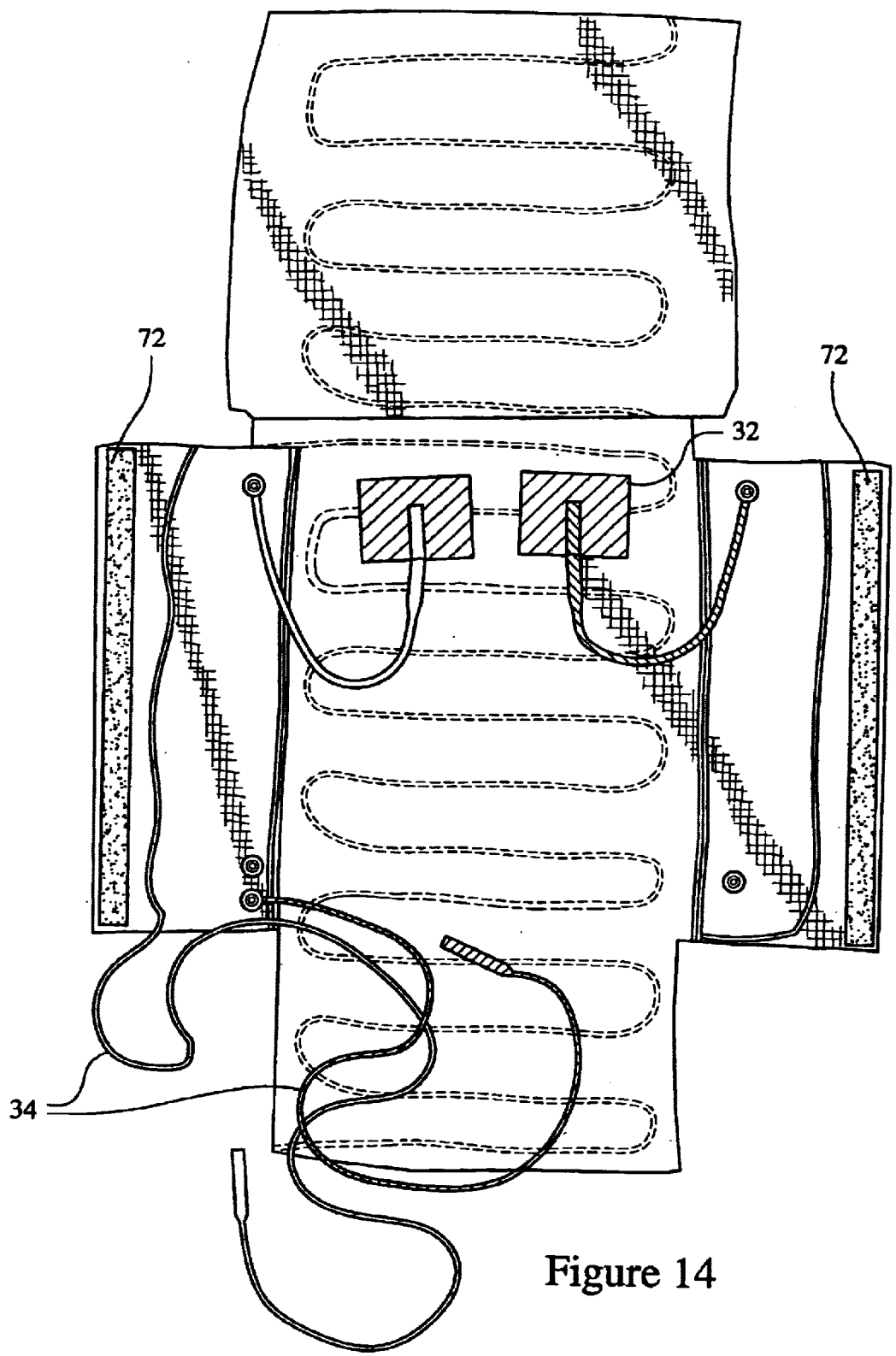
FIG. 14 illustrates the sensors and the connecting wires plugged into the embodiment in FIG. 11.

FIG. 11 is the front view of another embodiment of the present invention and FIG. 12 is an opened out view of the single piece integrated structure in FIG. 11. A hole (not shown in FIG. 12) is cut in the middle of the integrated piece so that the garment can be put on the infant by sliding the infant's head through it. The neck opening can be seen in FIG. 11. The data bus 50 is attached to one half (the front side) of the garment which also shows the VELCRO strips 64 for attaching it to the other half (back side) of the garment. FIG. 13 shows the back of the garment with VELCRO strips 70 into which the strips 72 on the front side will join to create a form-fitting garment for the infant. FIG. 14 shows the sensors 32 attached to the inside of the front part and the sensor connecting wires 34 plugged into the T-Connectors in the garment. The key differences between this single-piece embodiment and the previous one discussed in FIGS. 1–5 are that the data bus is on the front side, the closure VELCRO strips 70 are on the sides of the back of the garment and the garment closes from front to back. This latter embodiment has a smooth appearance in the front of the garment. However, the former embodiment is the preferred one from the viewpoint of ease of use, the greater degree of control in putting it on properly for the baby and overall comfort for the baby because the back will be smooth due to the absence of "ridges" that might be caused by the VELCRO attachments. This latter embodiment can be made optionally in two pieces and the shoulder joining/adjustment feature in the former embodiment (FIGS. 2 and 4) can be incorporated into it.

As noted earlier, zippers, buttons, hooks, sewing, gluing and other means can be used to join the front and back panels of all the embodiments of the present invention. Moreover, the arrangements of the various interfaces for attaching sensors and transmitting the data (the VELCRO strips, the T-Connectors, the lengths of the connecting wires, etc.) can be varied as desired and deemed beneficial. Similarly, provision can be made in the front panel of the garment to facilitate the ease of care of the umbilical cord of the newborn infant.

Suitable sensors include conventional hospital EKG sensors, temperature sensors, such as any thermistor type sensor, voice sensors such as any general purpose lapel microphone, and respiration rate sensors such as a Respi-Trace™ sensor.

2. Woven Fabric/Garment

While the preceding description has discussed knitting as the means for creating the embodiments for the present invention, weaving can also be used to create the fabric/garment 20 with the information infrastructure component integrated into the structure. An example of a woven garment having the information infrastructure integrated within the fabric, and a process for weaving the fabric for such a garment, is found in our co-pending U.S. application Ser. No. 09/157,607, filed Sep. 21, 1998, on which priority is claimed for our co-pending PCT application PCT/US98/19620 (International Publication No. WO 94/15722), which applications are incorporated herein by reference as if fully set forth herein.

Figure 16:
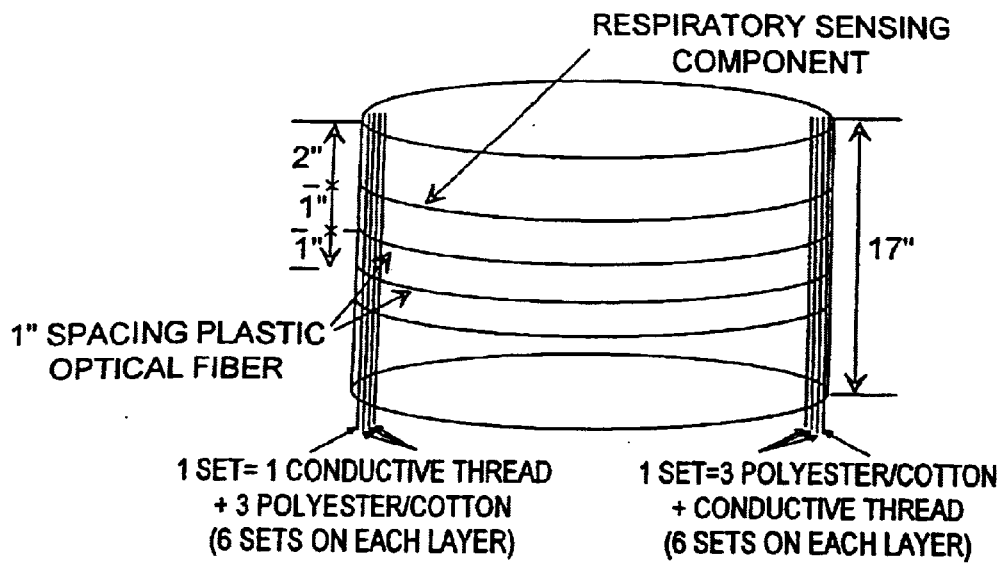
FIG. 16 illustrates a woven portion of a garment including the integrated information infrastructure according to one embodiment of the present invention.

FIG. 16 illustrates one embodiment of the fabric of the present invention consisting of a woven comfort component of polyester/cotton yarn. A data/power bus for carrying the sensor data or other information is integrated by weaving into the fabric twelve insulated conductive yarns spaced 5 mm apart on either side of the garment. In addition, one of the Respitrace Sensors is woven into the fabric as shown in FIG. 16. The signals from this chest level Respitrace sensor and another woven at the abdomen level are fed directly, or through a PSM (personal status monitor) described in more detail below, to a monitoring device to measure the breathing rate of the wearer. In the case of a temperature sensor, the type of sensor utilized is preferably a standard Thermistor Type Sensor. In the case of a voice sensor a lapel type microphone is preferably used. For EKG sensors, a standard type sensor used in conjunction with typical hospital equipment is preferably used.

Figure 17:
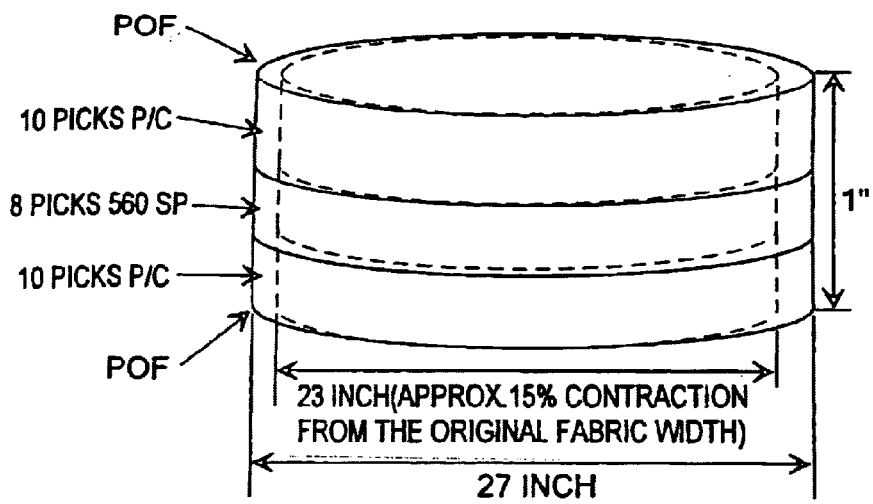
FIG. 17 illustrates a woven portion of a garment including the integrated information infrastructure according to another embodiment of the present invention.
Figure 18:
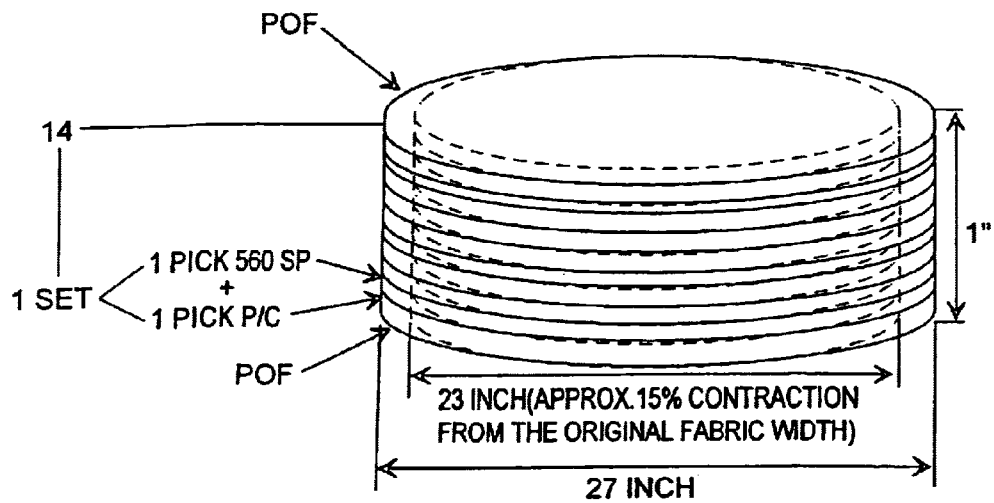
FIG. 18 illustrates a woven portion of a garment including the integrated information infrastructure according to a further embodiment of the present invention.
Figure 19:
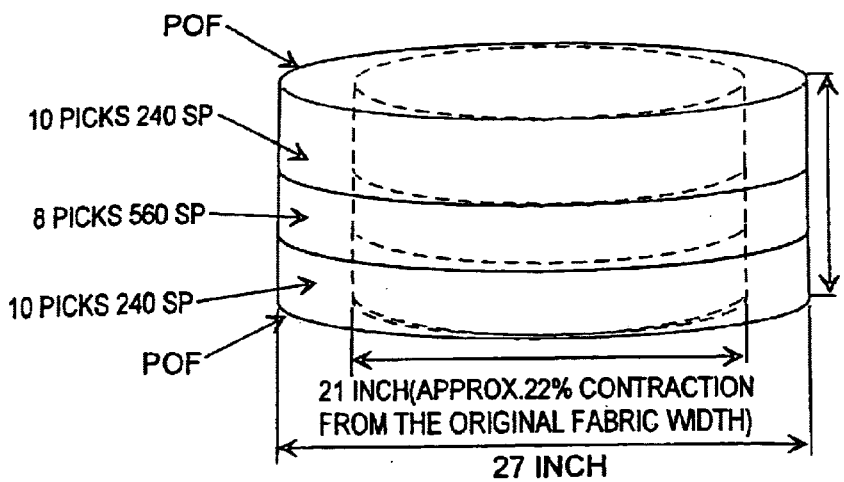
FIG. 19 illustrates a woven portion of a garment including the integrated information infrastructure according to another embodiment of the present invention.

FIGS. 17–19 illustrate additional embodiments of our fabric consisting of woven designs for form fit. The warp and filling yarns for these designs are given below.

| | Warp | | Filling | |
|---|---|---|---|---|
| | Material | EPI | Material | PPI |
| Design I (FIG. 17) | Polyester/Cotton | 30 | Polyester/Cotton | 10 |
| | | | 560 Denier Core-Spun SPANDEX | 8 |
| | | | Polyester/Cotton | 10 |
| Design II (FIG. 18) | Polyester/Cotton | 30 | Polyester/Cotton | 14 |
| | | | 560 Denier Core-Spun SPANDEX | 14 |
| Design III (FIG. 19) | Polyester/Cotton | 30 | 240 Denier Core-Spun SPANDEX | 10 |
| | | | 560 Denier Core-Spun SPANDEX | 8 |
| | | | 240 Denier Core-Spun SPANDEX | 10 |

Figure 20:
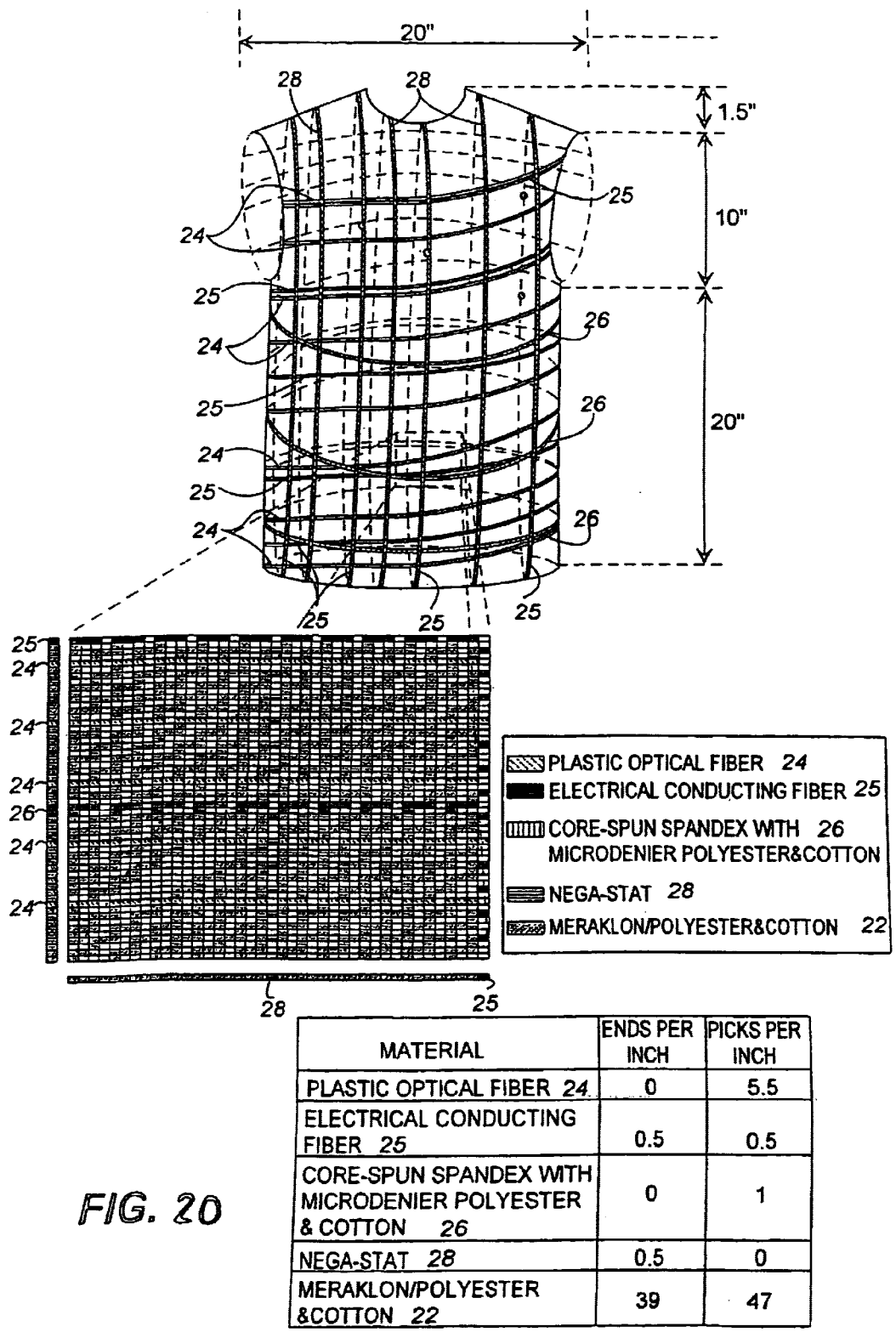
FIG. 20 illustrates a further embodiment of the present invention including the information infrastructure fashioned into a wearable garment.

FIG. 20 shows another representative design of the fabric of the present invention. It consists of a single-piece garment woven similar to a regular sleeveless T-shirt. The legend in the figure denotes the relative distribution of yarns for the various structural components of the fabric in a 2" segment.

The information infrastructure component of the woven fabric is shown as including materials 24 for sensing of the fabric 20, or materials 25 for sensing one or more body vital signs, or both. These materials are woven during the weaving of the comfort component of the fabric. After fashioning of the fabric into a garment is completed, these materials can be connected to a monitor (referred to earlier as a "personal status monitor" or "PSM") which will take readings from the sensing materials, monitor the readings and issue an alert depending upon the readings and desired settings for the monitor, as described in more detail below. As seen from the discussion above concerning the knitted embodiment of this invention, the materials for penetration detection need not be included where penetration detection is not desired. They may be included in the knitted embodiment if penetration detection is desired.

Materials suitable for providing penetration detection and alert include but are not limited to: silica-based optical fibers, plastic optical fibers, and silicone rubber optical fibers. Suitable optical fibers include those having a filler medium which have a bandwidth which can support the desired signal to be transmitted and required data streams. Silica-based optical fibers have been designed for use in high bandwidth, long distance applications. Their extremely small silica core and low numerical aperture (NA) provide a large bandwidth (up to 500 mhz*km) and low attenuation (as low as 0.5 dB/km). However, such fibers are currently not preferred because of high labor costs of installation and the danger of splintering of the fibers.

Plastic optical fibers (POF) provide many of the same advantages that glass fibers do, but at a lower weight and cost. In certain fiber applications, as in some sensors and medical applications, the fiber length used is so short (less than a few meters) that the fiber loss and fiber dispersion are of no concern. Instead, good optical transparency, adequate mechanical strength, and flexibility are the more important properties and plastic or polymer fibers are preferred. Moreover, plastic optical fibers do not splinter like glass fibers and, thus, can be more safely used in the fabric than glass fibers.

For relatively short lengths, POFs have several inherent advantages over glass fibers. POFs exhibit relatively higher numerical aperture (N.A.), which contributes to their capability to deliver more power. In addition, the higher N.A. lowers the POF's susceptibility to light loss caused by bending and flexing of the fiber. Transmission in the visible wavelengths range is relatively higher than anywhere else in the spectra. This is an advantage since in most medical sensors the transducers are actuated by wavelengths in the visible range of the optical spectra. Because of the nature of its optical transmission, POF offers similar high bandwidth capability and the same electromagnetic immunity as glass fiber. In addition to being relatively inexpensive, POF can be terminated using a hot plate procedure which melts back the excess fiber to an optical quality end finish. This simple termination combined with the snap-lock design of the POF connection system allows for the termination of a node in under a minute. This translates into extremely low installation costs. Further, POFs can withstand a rougher mechanical treatment displayed in relatively unfriendly environments. Applications demanding inexpensive and durable optical fibers for conducting visible wavelengths over short distances are currently dominated by POFs made of either poly-methyl-methacrylate (PMMA) or styrene-based polymers.

Silicone rubber optical fibers (SROF), a third class of optical fibers, provide excellent bending properties and elastic recovery. However, they are relatively thick (of the order of 5 mm) and suffer from a high degree of signal attenuation. Also, they are affected by high humidity and are not yet commercially available. Hence, these fibers are not currently preferred for use in the fabric.

In FIG. 20, the POF 24 is shown in the filling direction of the fabric, though it need not be limited to only the filling direction. To incorporate the penetration sensing component material into a tubular woven fabric, the material, preferably plastic optical fiber (POF), is spirally integrated into the structure during the full-fashioned weaving fabric production process as described in copending U.S. patent application Ser. No. 09/157,607, which is incorporated herein in its entirety as if fully set forth herein. The POF continues throughout the fabric without any discontinuities. This results in only one single integrated fabric and no seams are present in the garment. The preferred plastic optical fiber is from Toray Industries, New York, in particular product code PGS—FB250 optical fiber cord.

B. Interconnection of Electrical Conductive Fibers

Referring back to FIG. 10, interconnection of electrical conductive fibers incorporated into the fabric can be achieved by the following sequence of operations:

1. Softening and removal of the insulation of the electrical conductive fibers at the desired intersection zone;
2. Abrasion of insulation at the intersection zone;
3. Application of a conductive polymer paste at the intersection zone to establish the interconnection between the electrical conductive fibers;
4. Insulation of the interconnect zone to prevent undesirable short circuits; and
5. If desired, attachment of sensor or connector.

The potential for automation has been a key driving factor in the development of the interconnection process since automation is essential for large scale production of the fabric/garment. Also, automation is preferred for the reproducibility and repeatability of the various steps to create a uniform product on a continuous basis. The details of the various steps are presently discussed.

1. Softening and Removal of Insulation

In order to make a connection of intersecting electrical conductive fibers, the insulation at the intersection must first be removed. This can be done by any one of a number of ways. Suitable removal techniques include chemical etching, mechanical removal and any spot welding technique such as ultrasonic welding, laser light application or other localized heating technique. Preferably, the interconnection zone is chemically softened for the effective removal of the insulation, such as vinyl sheath. The process variables are: (i) the chemical used in the process; (ii) the concentration of the chemical; (iii) the amount of chemical applied; and (iv) duration of chemical application. Acetone has been found to work quite well as a chemical-softening agent. A few drops of Acetone are applied. It is allowed to stand for about 10 seconds before the next step in the process. These processing conditions ensure that the conductive yarn itself is not damaged. Also since polyester, cotton and SPANDEX do not interact with acetone, they are not damaged during this process. Where stainless steel is used as the electrical conductive fiber, heat alone may be sufficient to achieve the desired softening.

2. Abrasion of Insulation

Figure 10:
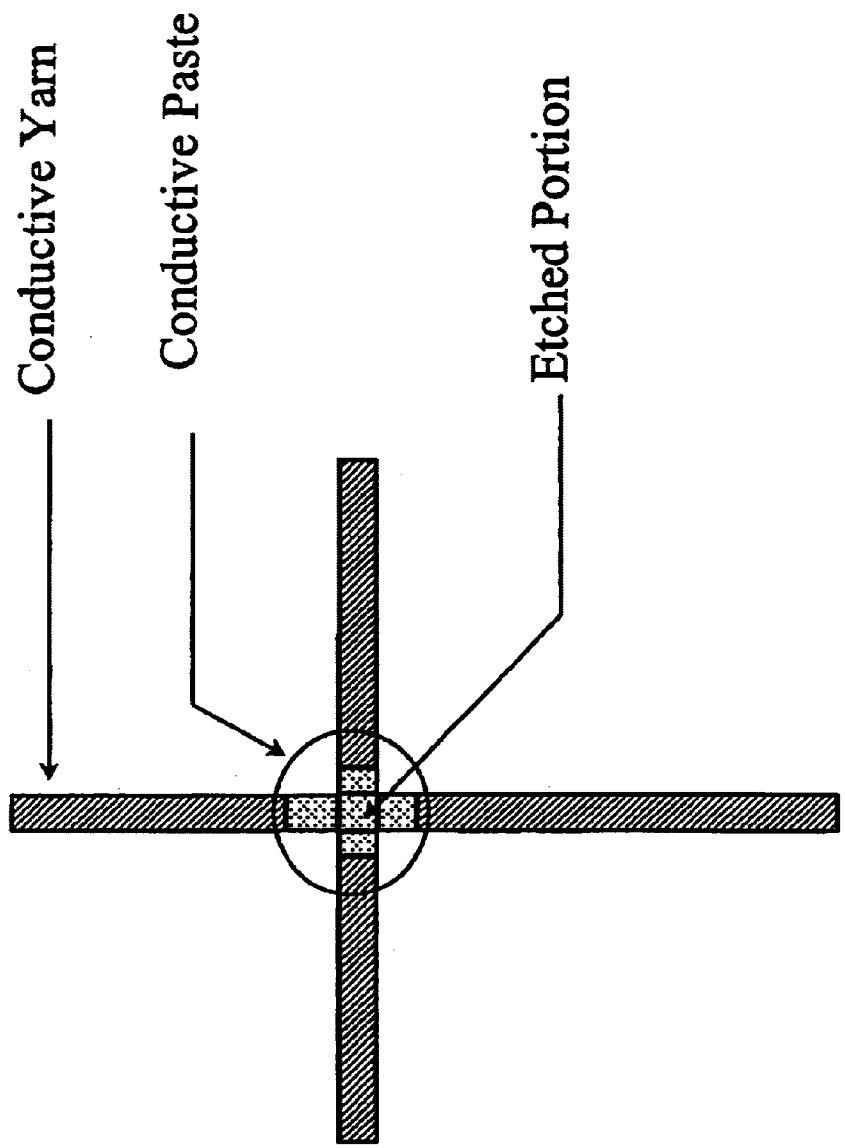
FIG. 10 illustrates another aspect of the present invention, namely, the interconnection of intersecting electrically conductive fibers in the fabric or garment of a preferred embodiment of the present invention.

The next step, if needed, is to abrade the insulation at the intersection zone that has been softened. A vibrating brush can be used, preferably one that oscillates at 3000 Hz. This effectively strips out the insulation at the interconnection zone as shown in FIG. 10. The process variables are: (i) the frequency of oscillation of the brush; (ii) the pressure applied during abrasion; and (iii) duration of abrasion. By modifying these parameters, it would be possible to strip out different types of insulation without damaging the conductive yarns themselves. Depending on the method used for removal of insulation, it may or may not be necessary to carry out this step. Some methods of removal may result in removal of sufficient amount of insulation such that this abrasion step would not be needed.

3. Application of Conductive Paste

The interconnection between the conductive yarns where the insulation has been removed can be established by applying a conductive paste to close the circuit between the conductive yarns. The process variables are: (i) the properties of the conductive paste used in the process; and (ii) the quantity of the paste applied to the interconnect zone. The conductive paste should be chosen such that it offers only minimum electrical resistance, adheres well to the conductive yarns, and does not chemically react with the conductive yarn. Based on these requirements, Magnolia 3870, a silver-filled epoxy, room temperature curing paste, is a preferred conducting paste. It has a shear strength of 2000 psi at 75° F. and has a resistivity of 0.004 ohm-cm at 75° F. It also cures well at room temperature and does not react with the polyarnide conductive yarn. It can be applied to the interconnect zone using a grease gun or a similar device.

4. Insulation of the Interconnection Zone

The interconnection zone must be insulated to prevent it from shorting. A polyester/urethane based resin can be used to insulate the interconnection zone. The insulating layer should not chemically react with the conductive paste, should adhere well to the paste and should offer adequate insulation. It can be applied to the interconnection zone using a brush or other application means.

5. Attachment of a Sensor or Sensor Connector

Additionally, if desired, either a sensor or a sensor connector, such as a T-Connector, can be attached to the interconnection zone. FIG. 4 shows the interconnection point 46 and the sets of T-Connectors 42, and 44, respectively. FIGS. 8 and 9 illustrate the use of the T-Connectors for carrying the sensor data to monitoring equipment through the garment of the present invention.

Yet another modification is to provide a keyboard capability in the garment using either the conducting fibers themselves or through sensors mounted on the conducting fibers using the interconnection technology so that the keyboard can serve as an input device for the information processing and monitoring devices plugged into the fabric of our present invention.

C. Core Spinning Technology

Core spinning is the process of sheathing a core yarn (e.g., SPANDEX yarns) with sheath fibers (e.g., Cotton or Polyester/Cotton). It is not required in all situations for the present invention. It is desirable when the information infrastructure component, or other components other than the comfort component, do not possess the comfort properties that are desired for the garment. There are two ways to core spin yarns—one using modified ring spinning machines and another by using a friction-spinning machine. Ring spinning machines are very versatile and can be used for core spinning both fine and coarse count yarns. However, the productivity of the ring-spinning machine is low and the package sizes are very small. Friction spinning machines can be used only to produce coarse count yarns, but the production rates and the package sizes are much higher than ring spinning. Where the yarns that are used are relatively coarse, friction-spinning technology is preferred for core spinning the yarns.

The preferred configuration of the friction-spinning machine for producing core spun yarns is as follows:

| Parameter | Details |
|---|---|
| Machine Model | DREF3 ® |
| Machine Description | Friction Core Spinning Machine |
| Draft | 200 |
| Speed | 170 m/in |
| Number of Doublings | 5 |
| Drafting Mechanism Type | 3/3 |
| Core-Sheath Ratio | 50:50 |

A full-scale prototype of the knitted garment of the present invention was produced. Although both the embodiments discussed earlier were created, the former (FIGS. 1–5) is the preferred one.

The presently used PSM is a cardiorespiratory monitoring equipment from Respironics, Inc. into which the connecting wires 34 from the garment are plugged to carry and record the sensor data (FIG. 6). Alternatively, and preferably, the PSM should be a light weight device that is preferably located at the hip/waist level of the infant, i.e. at the bottom of the garment and away from the chest level with the sensor wires. The information obtained by this pager-like PSM (e.g., heart rate, respiration, etc.) should be transmitted to a remote control center (e.g., medical personnel at a monitoring station and/or in a hospital) whenever a preset threshold for apnea/bradycardia is exceeded while simultaneously alerting the caregiver. The information transfer can occur through Broadband-Code Division Multiplexing or other appropriate wireless data transmission techniques known in the art. The transmitter can be built into the PSM or attached to the PSM or can be located externally on the outer garment of the user and coupled to the PSM using wire conductors or other appropriate means. FIG. 6 provides the overall architecture of the garment of the present invention.

D. Operation of the Fabric (Garment) With Integrated Information Infrastructure The operation of our above-described fabric/garment having an integrated information infrastructure to illustrate its vital signs monitoring capabilities and without any risk of wrapping of wires around the baby is now discussed.

Vital Signs Monitoring:

1. The back panel is laid on the surface (e.g., a table or crib) with the flaps 52 spread out. The baby (without any clothes on the chest) is placed on its back on the back panel.
2. The cardiorespiratory sensors 32 are attached to the VELCRO strips 68 on the front panel as shown in FIG. 3. The connecting wires 34 are attached to the sensors.
3. The front panel with the sensors and the connecting wires is placed on the baby's chest. The connecting wires 34 from the sensors are plugged into the top set of T-Connectors 42 on the flaps 52 of the back panel.
4. The second set of connecting wires 34 is plugged into the bottom set of T-Connectors 44 on the left flap 52 of the back panel; the other ends of the connecting wires are let down through the bottom of the garment.

5. The two flaps are closed and VELCRO 64 is bound to VELCRO 60 on the front piece to ensure a snug fit so that the sensors stay in place to minimize the risk of false alarms while the baby is comfortable. This feature also helps to extend the usable life of the garment as the baby grows.
6. The shoulder VELCRO strips 62 and 66 in the front and back panels, respectively, are used to adjust the shoulder length to ensure a proper fit for the baby.
7. The bottom closures 90 and 92 are used to join the two pieces at the lower end to create an integrated garment.
8. The two free ends of the connecting wires 34 are hooked up to the cardiorespiratory monitor and the monitor is turned on.
9. The heart rate and breathing rate signals from the two sensors travel through the set of connecting wires attached to the sensors, through the top set of T-Connectors, through the electrical conducting component, through the data bus, to the set of T-Connectors at the bottom of the garment, through the second set of connecting wires plugged into these T-Connectors and to the cardiorespiratory monitor.
10. If the signals from the sensors are within the normal range, no specific action other than continuous recording and erasing of the data occurs.
11. If the signals from the sensors are outside the preset threshold levels for apnea and/or bradycardia, two functions occur. First, the monitor emits a loud alarm to warn the caregiver of a problem. Second, the monitor records the EKG, trend event of the heart rate, and the respiratory waveforms. This data can then be downloaded via telephone modem to verify the event at a remote monitoring location or hospital by appropriate medical personnel.

Thus, the fabric/garment of our present invention is easy to deploy and meets all the functional requirements for monitoring vital signs of infants. Moreover, the risk of the infant being wrapped around by the wires is eliminated in the design. Thus this invention will help in the reduction and/or prevention of fatalities due to SIDS. Additional applications include safety activities where it is desirable to maintain updates on the physical condition and location of the infant. By combining the physical sensors with GPS (Global Positioning System), the location and physical signals for the infant can be monitored, thereby increasing the infant's safety.

Just as the home security industry is a big business that monitors and protects homes, our fabric having an integrated information infrastructure has the potential to spawn a new industry for the reliable and effective monitoring of infants at home and thereby transform home healthcare delivery.

Further, the fabric/garment can also transmit signals that are received by receivers coupled to the data buses or the PSM. The fabric/garment can utilize separate buses for transmitting and receiving signals if a certain bandwidth is needed for the received signals.

The advantages of incorporating the receive and transmit functions into the single garment include reduction in the amount of equipment on the infant., In addition to transmitting the vital signs data of the infant, specially designed sensors can act as receivers of external signals (e.g., from the PSM) through the electrical conducting component (data bus) in the fabric/garment. For example, this feature can be used to automatically stimulate (rock/shake) an infant experiencing apnea and/or bradycardia. These signals can include video, positional signals, information on other members of a group, etc. The information can be transmitted utilizing B-CDMA or other communication protocols. For instance, the received signals can, for instance, be voice signals sent through the garment to an ear piece worn by the user. Video data can be supplied to a monitor that is coupled to garment or flat screen display that is attached to the garment. The fabric/garment can utilize separate buses for transmitting and receiving signals if a certain bandwidth is needed for the received signals. Also, this feature can be used to modify the sensitivity of the sensors as needed. Thus, the fabric/garment pioneers the class of adaptive and responsive textile structures (ARTS). A related application of the fabric is to interact with Java™ or similarly enabled devices and appliances to enhance the overall healthcare delivery for infants, especially those susceptible to SIDS.

The fabric/garment allows a new way to customize information processing devices to "fit" the wearer by selecting and plugging in (or removing) chips/sensors from the garment, thus creating a wearable information infrastructure.

While the invention has been disclosed in its preferred forms, it will be apparent to those skilled in the art that many modifications, additions, and deletions can be made therein without departing from the spirit and scope of the invention and its equivalents as set forth in the following claims.

What is claimed:

1. A garment for infants comprising:

a comfort component serving as a base of a fabric;

an information infrastructure component integrated within the comfort component to form the fabric, the information infrastructure component comprising individually insulated conductive fibers, wherein one or more of said individually insulated conductive fibers interconnect; and at least one interface that provides a transmission path between the information infrastructure component and an external device.

2. A garment as defined in claim 1, wherein the comfort component is a yarn selected from the group consisting of fibers of cotton, polyester, cotton/polyester blends, and microdenier polyester/cotton blends, and combinations thereof.

3. A garment as defined in claim 1, wherein the information infrastructure component is selected from the group consisting of insulated and intrinsically conducting polymers, doped fibers, metallic fibers, and optical fibers, and combinations thereof.

4. A garment as defined in claim 1, wherein the comfort component is selected from the group consisting of two-dimensional woven and knitted fabrics, tubular woven and knitted fabrics and fully-fashioned woven and knitted garments.

5. A garment as defined in claim 1 further comprising means for adjusting the size of the garment.

6. A garment as defined in claim 1 wherein said at least one interface comprises a plurality of interfaces and said garment further comprising sensors that measure vital signs such as heart rate and breathing rate and said sensors coupled separately to said plurality of interfaces.

7. A garment as defined in claim 6 further comprising a cardiorespiratory monitoring device coupled to an interface of said plurality of interfaces.

8. A garment as defined in claim 7 wherein the interface through which said cardiorespiratory monitoring device is coupled to said garment is located below the ports that couple said sensors that measure heart rate and breathing rate.

9. A fabric comprising:

a comfort component serving as a base of the fabric;

an information infrastructure component integrated within the comfort component to form the fabric, the information infrastructure component comprising individually insulated conductive fibers, wherein one or more of said individually insulated conductive fibers interconnect; and at least one interface that provides a transmission path between the information infrastructure component and an external device.

10. A fabric as defined in claim 9 further comprising at least one hook and loop-type fastener attachment for attaching the fabric panels to form a garment that can be worn by an infant.

11. A fabric as defined in claim 9 further comprising means for coupling the fabric to form a garment that can be worn by an infant.

12. A fabric as defined in claim 9, wherein the comfort component is a yarn selected from the group consisting of fibers of cotton, polyester, cotton/polyester blends, and microdenier polyester/cotton blends, and combinations thereof.

13. A fabric as defined in claim 9, wherein the information infrastructure component is selected from the group consisting of insulated and intrinsically conducting polymers, doped fibers, metallic fibers, and optical fibers, and combinations thereof.

14. A fabric as defined in claim 9, wherein the comfort component is selected from the group consisting of two-dimensional woven and knitted fabrics and tubular woven and knitted fabrics.

15. A garment for infants comprising:

a comfort component serving as a base;

a plurality of signal transmission paths integrated within the comfort component to form a fabric, said signal transmission paths comprising individually insulated conductive fibers, wherein one or more of said individually insulated conductive fibers interconnect; and at least one interface that sends signals to or receives signals from an external device.

16. A garment as defined in claim 15, wherein said plurality of signal transmission paths are woven into said comfort component.

17. A garment as defined in claim 15, wherein said plurality of signal transmission paths arc knitted into said comfort component.

18. A garment as defined in claim 15, further comprising means for adjusting the size of the garment.

19. A garment as defined in claim 15 comprising a plurality of ports, said garment further comprising sensors that measure vital signs with the said sensors coupled to separate ports of said plurality of ports, and a monitoring device coupled to one of the ports of said plurality of ports.

20. A garment as defined in claim 19, wherein the port through which said monitoring device coupled to said garment is located below the ports that couple said sensors that measure vital signs.

21. A garment for infants as defined in claim 1, further comprising a penetration sensing component, a sensor, a processor, or a wireless transmission device.

22. A fabric as defined in claim 9, further comprising a penetration sensing component, a sensor, a processor, or a wireless transmission device.

23. A garment for infants as defined in claim 15, further comprising a penetration sensing component, a sensor, a processor, or a wireless transmission device.

* * * * *

UNITED STATES PATENT AND TRADEMARK OFFICE
CERTIFICATE OF CORRECTION

PATENT NO. : 6,687,523 B1
DATED : February 3, 2004
INVENTOR(S) : Sundaresan Jayaraman et al.

It is certified that error appears in the above-identified patent and that said Letters Patent is hereby corrected as shown below:

Title page,
Item [75], first inventor's name should read -- Sundaresan Jayaraman --

Signed and Sealed this

Sixth Day of April, 2004

JON W. DUDAS
*Acting Director of the United States Patent and Trademark Office*